US010849899B2

(12) United States Patent
Lindmark et al.

(10) Patent No.: US 10,849,899 B2
(45) Date of Patent: *Dec. 1, 2020

(54) COMBINATION THERAPY COMPRISING VARLITINIB AND AN ANTICANCER AGENT

(71) Applicant: ASLAN Pharmaceuticals PTE LTD, Singapore (SG)

(72) Inventors: Bertil Lindmark, Singapore (SG); Lisa Ooi, Singapore (SG)

(73) Assignee: ASLAN Pharmaceuticals PTE LTD, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/508,444

(22) Filed: Jul. 11, 2019

(65) Prior Publication Data
US 2020/0009144 A1   Jan. 9, 2020

Related U.S. Application Data

(63) Continuation of application No. 15/757,133, filed as application No. PCT/EP2016/070888 on Sep. 5, 2016, now Pat. No. 10,357,494.

(60) Provisional application No. 62/217,332, filed on Sep. 11, 2015, provisional application No. 62/217,346, filed on Sep. 11, 2015.

(30) Foreign Application Priority Data

| Sep. 4, 2015 | (GB) | 1515712.6 |
| Sep. 4, 2015 | (GB) | 1515714.2 |
| Sep. 4, 2015 | (GB) | 1515716.7 |
| Sep. 4, 2015 | (GB) | 1515718.3 |
| Apr. 1, 2016 | (GB) | 1605583.2 |
| May 17, 2016 | (GB) | 1608660.5 |

(51) Int. Cl.
| *C07D 239/94* | (2006.01) |
| *A61K 31/517* | (2006.01) |
| *A61P 35/00* | (2006.01) |
| *A61K 31/51* | (2006.01) |
| *A61K 9/00* | (2006.01) |
| *A61K 31/7068* | (2006.01) |
| *A61K 33/24* | (2019.01) |
| *A61K 31/282* | (2006.01) |
| *A61K 31/513* | (2006.01) |

(52) U.S. Cl.
CPC .......... *A61K 31/517* (2013.01); *A61K 9/0053* (2013.01); *A61K 31/51* (2013.01); *A61K 31/7068* (2013.01); *A61K 33/24* (2013.01); *A61P 35/00* (2018.01); *C07D 239/94* (2013.01); *A61K 31/282* (2013.01); *A61K 31/513* (2013.01); *A61K 2300/00* (2013.01)

(58) Field of Classification Search
CPC ..... C07D 239/94; A61K 31/517; A61P 35/00; A61P 31/517

USPC ................ 544/284, 293, 283; 514/266.2
See application file for complete search history.

(56) References Cited

U.S. PATENT DOCUMENTS

| 7,452,895 B2 | 11/2008 | Wallace |
| 10,357,494 B2* | 7/2019 | Lindmark .......... A61K 31/7068 |
| 2015/0086541 A1 | 3/2015 | Aguilar-Cordova |
| 2018/0243302 A1 | 8/2018 | Lindmark et al. |
| 2018/0256578 A1 | 9/2018 | Lindmark et al. |
| 2018/0353510 A1 | 12/2018 | Lindmark et al. |
| 2019/0117655 A1 | 4/2019 | Lindmark et al. |
| 2019/0134034 A1 | 5/2019 | Ooi et al. |
| 2019/0321365 A1 | 10/2019 | Lindmark |
| 2020/0009144 A1 | 1/2020 | Lindmark et al. |

FOREIGN PATENT DOCUMENTS

| EP | 2 963 114 A1 | 1/2016 |
| WO | 2005/016346 A1 | 2/2005 |
| WO | 2008/094484 A2 | 8/2008 |
| WO | 2008/122779 A1 | 10/2008 |
| WO | 2010/127417 A2 | 11/2010 |
| WO | 2013/112942 A1 | 8/2013 |
| WO | 2014/022138 A2 | 2/2014 |
| WO | 2015/027915 A1 | 3/2015 |
| WO | 2015/061752 A1 | 4/2015 |
| WO | 2015/153514 A1 | 10/2015 |
| WO | 2016/065330 A1 | 4/2016 |
| WO | 2017/037292 A1 | 3/2017 |
| WO | 2017/037298 A1 | 3/2017 |
| WO | 2017/037299 A1 | 3/2017 |
| WO | 2017/037300 A1 | 3/2017 |
| WO | 2017/184086 A1 | 10/2017 |
| WO | 2017/223275 A1 | 12/2017 |
| WO | 2018/004465 A1 | 1/2018 |

(Continued)

OTHER PUBLICATIONS

Cecil Textbook of Medicine, edited by Bennet, J.C., and Plum F., 20th edition,vol. 1, 1004-1010, 1996.*

(Continued)

*Primary Examiner* — Venkataraman Balasubramanian

(74) *Attorney, Agent, or Firm* — Prismatic Law Group, PLLC

(57) ABSTRACT

In one aspect the present disclosure provides a method of sensitizing a cancer patient to chemotherapy by administering a combination therapy comprising;

a) a therapeutically effective amount of a compound of formula (I) an enantiomer thereof or a pharmaceutically acceptable salts of any one of the same, and b) a chemotherapeutic agent or a combination of chemotherapeutic agents.

19 Claims, 16 Drawing Sheets

(56) References Cited

FOREIGN PATENT DOCUMENTS

| WO | 2019/083455 A1 | 5/2019 |
|---|---|---|
| WO | 2019/083456 A1 | 5/2019 |
| WO | 2019/083457 A1 | 5/2019 |
| WO | 2019/083458 A1 | 5/2019 |

OTHER PUBLICATIONS

Freshney et al.,Culture of Animal Cells, a Manual of Basic Technique, Alan R. Liss, Inc., 1983, New York, p. 4.*
Dermeret al., Bio/Technology, 1994, 12:320.*
Golub et al., Science, 286, 531-537, 1999.*
Cancer Drug Design and Discovery Neidle, Stephen, ed. (Elsevier/Academic Press, 2008) pp. 427-431.*
Appendix—Cancer Oct. 17, 2019.*
Ellard et al., Abstract #3603: ARRY-334543 in ErbB2 positive metastatic breast cancer and other ErbB expressing-cancers: experience from expansion cohorts on a phase I study, American Association of Cancer Research, AACR Annual Meeting, Apr. 18-22, 2009, Denver, CO, 3 pages.
International Search Report and Written Opinion, International Application No. PCT/EP2016/070888 (published as WO 2017/037298), dated Dec. 1, 2016, 9 pages.
Varlitinib, Database PubChem Compound, NCBI Database accession No. 42642648, Jul. 20, 2009.
Wang et al., ARRY-334543 Reverses Multidrug Resistance by Antagonizing the Activity of ATP-Binding Cassette Subfamily G Member 2, Journal of Cellular Biochemistry, vol. 115, No. 8, pp. 1381-1391 (Aug. 2014).
Lee et al., "In vivo activity of ARRY-543, a potent, small molecule inhibitor of EGFR/ErbB-2 in combination with tastuzumab or docetaxel." Cancer Res 69 (2 Suppl), Abstract #2150 (Jan. 2009).
Myers, "Array BioPharma's ARRY-543 Shows Potential Clinical Benefit in Cancer Patients," FierceBiotech (Apr. 23, 2009).
Kim et al., 664P: Phase IIA study to evaluate the biological activity of ASLAN001 in HER-1/2 co-expressing or HER-2 amplified advanced gastric cancer, Annals of Oncology, vol. 25, No. Supp 4, p. iv225 (2014).
Anonymous, "ASLAN Pharmaceuticals receives orphan drug designation from FDA for ASLAN001 (varlitinib) in cholangiocarcinoma," Aslan Pharmaceuticals, Aug. 13, 2015.
Anonymous, "ASLAN pharmaceuticals reports positive top-line results for phase 2 clinical trial of varlitinib in metastatic breast cancer—second-line treatment with varlitinib demonstrated significant tumour shrinkage in HER2-postiive breast cancer patients," Aslan Pharmaceuticals, Feb. 9, 2017.
Asian Scientist, "ASLAN's Bile duct cancer drug given FDA orphan drug status," Aug. 19, 2015.
Array Biopharma, Dr. Eli Wallace, "Selective inhibitors of the ErbB-family of receptor tyrosine kinase," Apr. 2, 2011.
Ooi et al, "Varlitinib demonstrates potent antitumor efficacy in patient-derived gastric cancer xenograft models," Proceedings of the American Association for Cancer Research 107th annual meeting, Cancer research, Apr. 20, 2016, vol. 76, No. 14 (supp), Abstract No. 4719.
Myers, "Array Biopharma's ARRY-543 shows potential clinical benefit in cancer patients," Apr. 23, 2009, FierceBiotech.
Blackwell et al, "Pan-ErbB inhibition by ARRY-334543 is superior to selective ErbB inhibition in a preclinical model that signals through multiple ErbB receptors," Proceedings of the American Association for Cancer Research Annual Meeting 101st meeting, Cancer Research, Apr. 21, 2010, vol. 70, No. 8 (supp), Abstract No. 3610.
Bushey, "ASLAN pharmaceuticals gains orphan designation for rare cancer drug," Rdmag, available at https://www.rdmag.com/news/2015/08/aslan-pharmaceuticals-gains-orphan-designation-rare-cancer-drug, Aug. 19, 2015.
Anderson et al, "In vivo activity of ARRY-334543, a potent, small molecule inhibitor of EGFR/ErbB2 in combination with trastuzumab or docetaxel," Proceedings of the American Association for Cancer Research Annual Meeting, Cancer Research, Apr. 18 to 22, 2009.
Deng et al, "Chemotherapy and target therapy for hepatocellular carcinoma: New advances and challenges," World Journal of Hepatology, Apr. 18, 2015, vol. 7, No. 5, 787-798.
Ellard et al, "Abstract #3603: ARRY-334543 in ErbB2 positive metastatic breast cancer and other ErbB expressing cancers: experience from expansion cohorts on a phase 1 study," Proceedings of the American Association for Cancer Research Annual Meeting, Cancer Research, Apr. 18 to 22, 2009.
Hirsch et al, "Epidermal growth factor receptor inhibition in lung cancer: status 2012," Journal of Thoracic Oncology, Mar. 1, 2013, vol. 8, No. 3, 373-384.
Jänne et al, "Phase I dose-escalation study of the pan-HER inhibitor, PF299804, in patients with advanced malignant solid tumors," Clinical cancer research, Mar. 1, 2011, vol. 17, No. 5, 1131-1139.
Kim et al, "664P: Phase IIa study to evaluate the biological activity of ASLAN001 in HER-1/2 co-expressing or HER-2 amplified advanced gastric cancer," Annals of Oncology, vol. 25, Sup 4, 2014, iv226.
Database PubChem accession No. 42642648, Varlitinib, created Jul. 20, 2009, modified Dec. 3, 2016.
Lee et al, "In vivo activity of ARRY-543, a potent, small molecule inhibitor of EGFR/ErbB-2 in combination with trastuzumab or docetaxel," Cancer Research, vol. 69, No. 2, suppl. S, Jan. 2009, 200s.
Nam et al, "The irreversible pan-HER inhibitor PF00299804 alone or combined with gemcitabine has an antitumor effect in biliary tract cancer cell lines," Investigational New Drugs, Dec. 25, 2011, vol. 30, No. 6, 2148-2160.
Nehls et al, "Capecitabine plus oxaliplatin as first-line treatment in patients with advanced biliary system adenocarcinoma: a prospective multicentre phase II trial," British Journal of Cancer, vol. 98, No. 2, Jan. 8, 2008.
Rothenberg et al, "A Phase I study of ARRY-543, a potent, selective reversible inhibitor of ErbB receptors," International Conference: Molecular Targets and Cancer Therapeutics, Oct. 26, 2007, Abstract No. B257.
Shuen et al, "Varlitinib demonstrates tumor regression and vessel normalisation in ErbB-dependent and mutated beta-catenin hepatocellular carcinoma patient-derived xenograft model," Cancer research, vol. 78, No. 13, supplement 1, Jul. 1, 2018.
Wang et al, "ARRY-334543 reverses multidrug resistance by antagonizing the activity of ATP-binding cassette subfamily G member," Journal of Cellular Biochemistry, Aug. 2014, vol. 115, No. 8, 1381-1391.
Wang et al, "The potential of panHER inhibition in cancer," Frontiers in Oncology, Jan. 28, 2015, vol. 5, article 2, 1-12.
Zhang et al, "Preclinical assessment of simultaneous targeting of epidermal growth factor receptor (ERBB1) and ERBB2 as a strategy for cholangiocarcinoma therapy", Hepatology, Sep. 2010, vol. 52, No. 3, 975-986.
Journal of Clinical and Experimental Medicine, Sep. 5, 2009, vol. 230, No. 10, pp. 911 to 917.
Journal of Clinical Surgery, Jul. 2009, vol. 64, No. 7, pp. 911 to 917.
Japanese Journal of Clinical Medicine, 2011, vol. 69, No. 3, pp. 433 to 438.
Partial Translation of Japanese Cited Documents, created for Japanese Patent Application No. 2018-511226, 1 page (Aug. 2020).

* cited by examiner

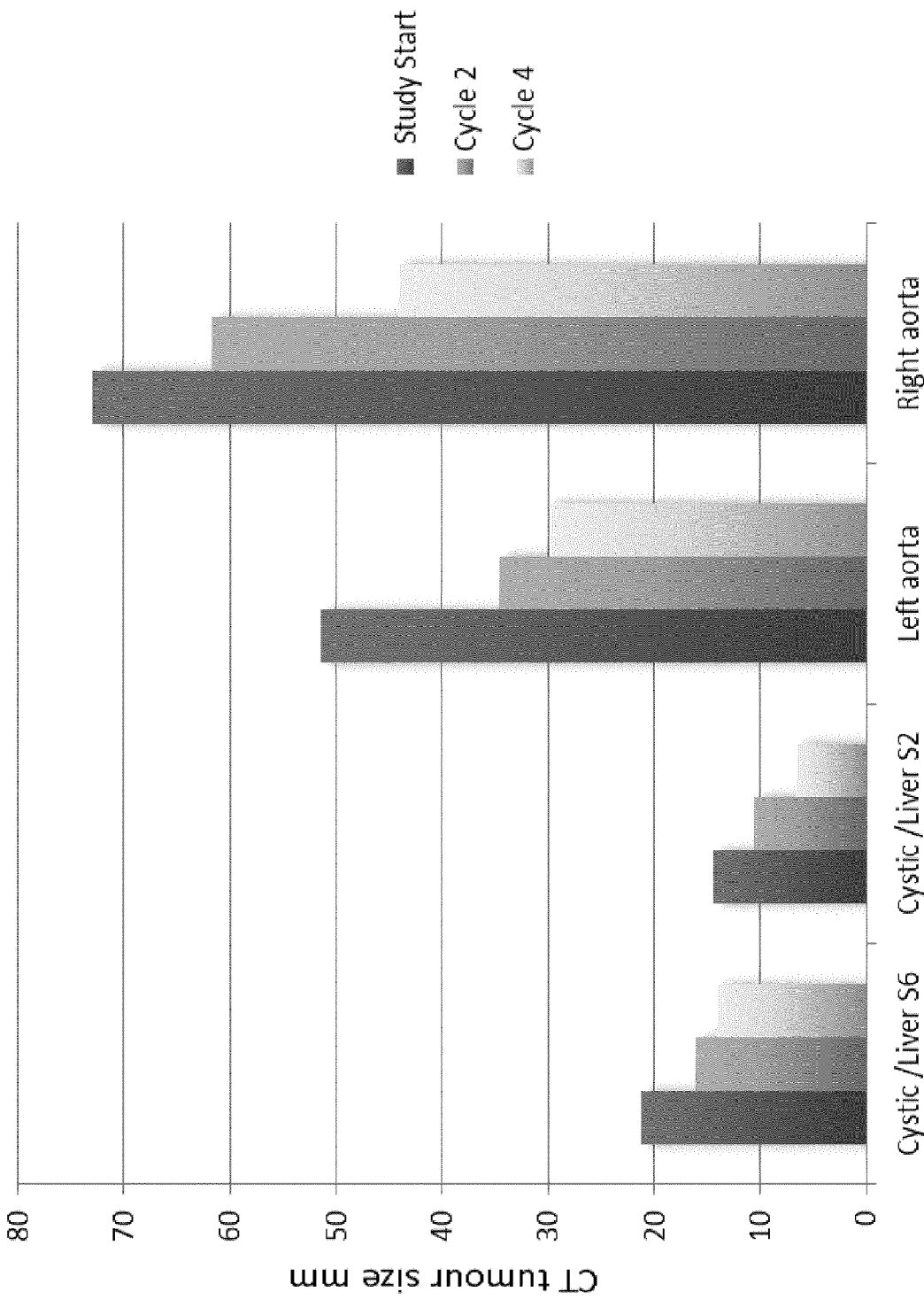
Figure 2  Varlitinib 400mg BID + Cispaltin/Capecitabine-46 year-old female

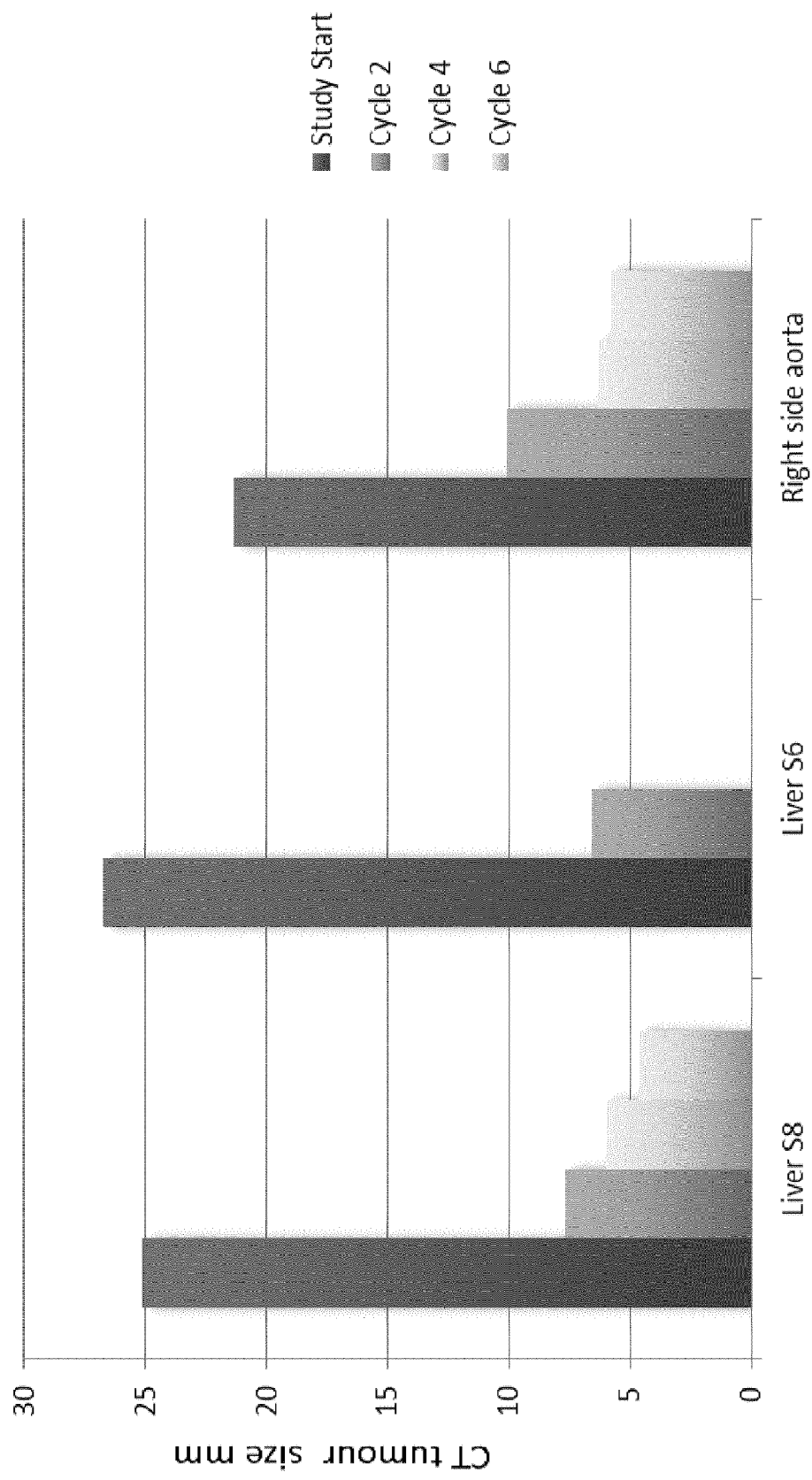
Figure 3  Valitinib 400mg BID + Cispaltin/Capecitabine-56 year-old male

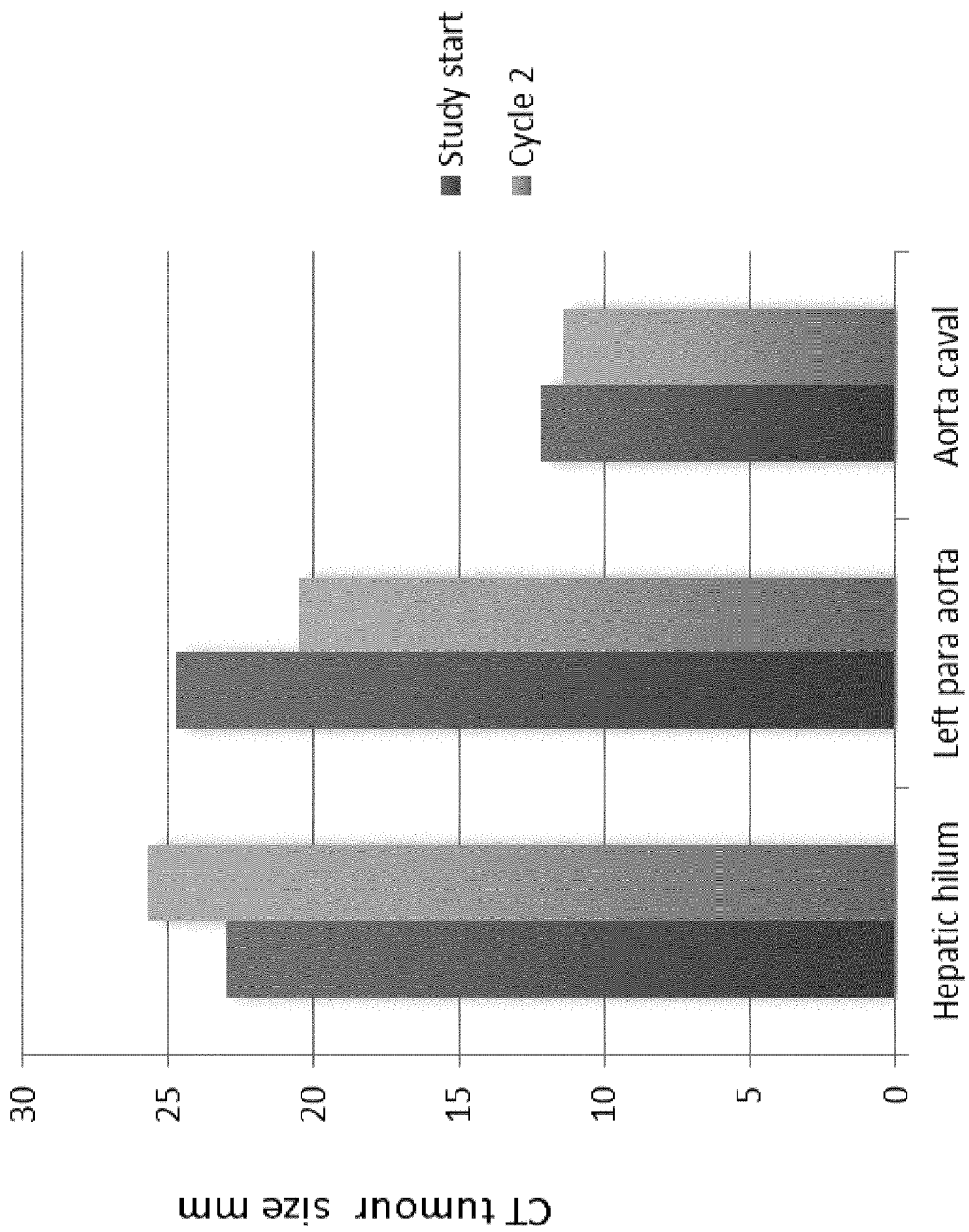
Figure 4  Varlitinib 500mg BID + Cispaltin/Capecitabine-60 year-old male

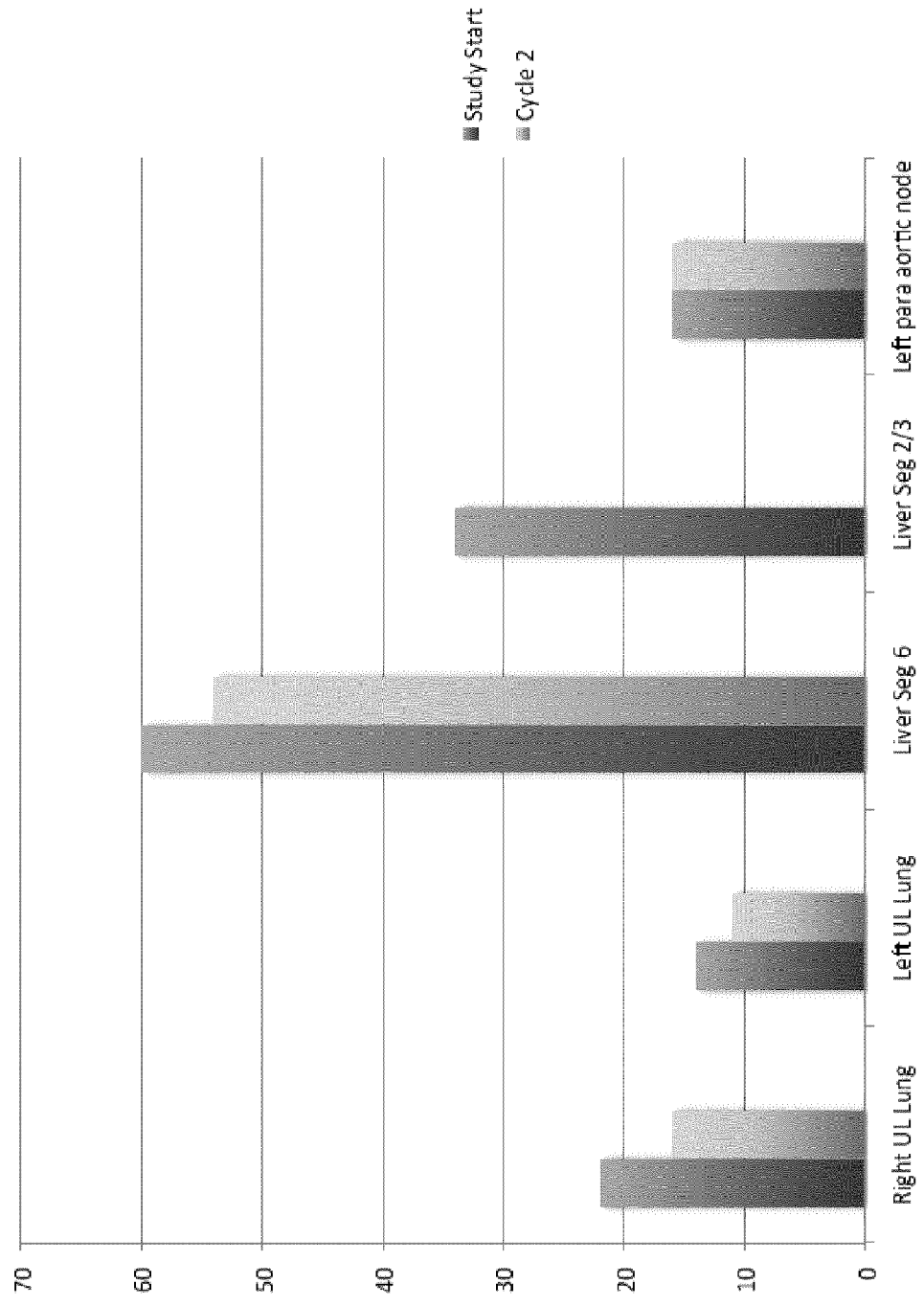
Figure 5  Varlitinib 300mg BID + Oxaliplatin/Capecitabine

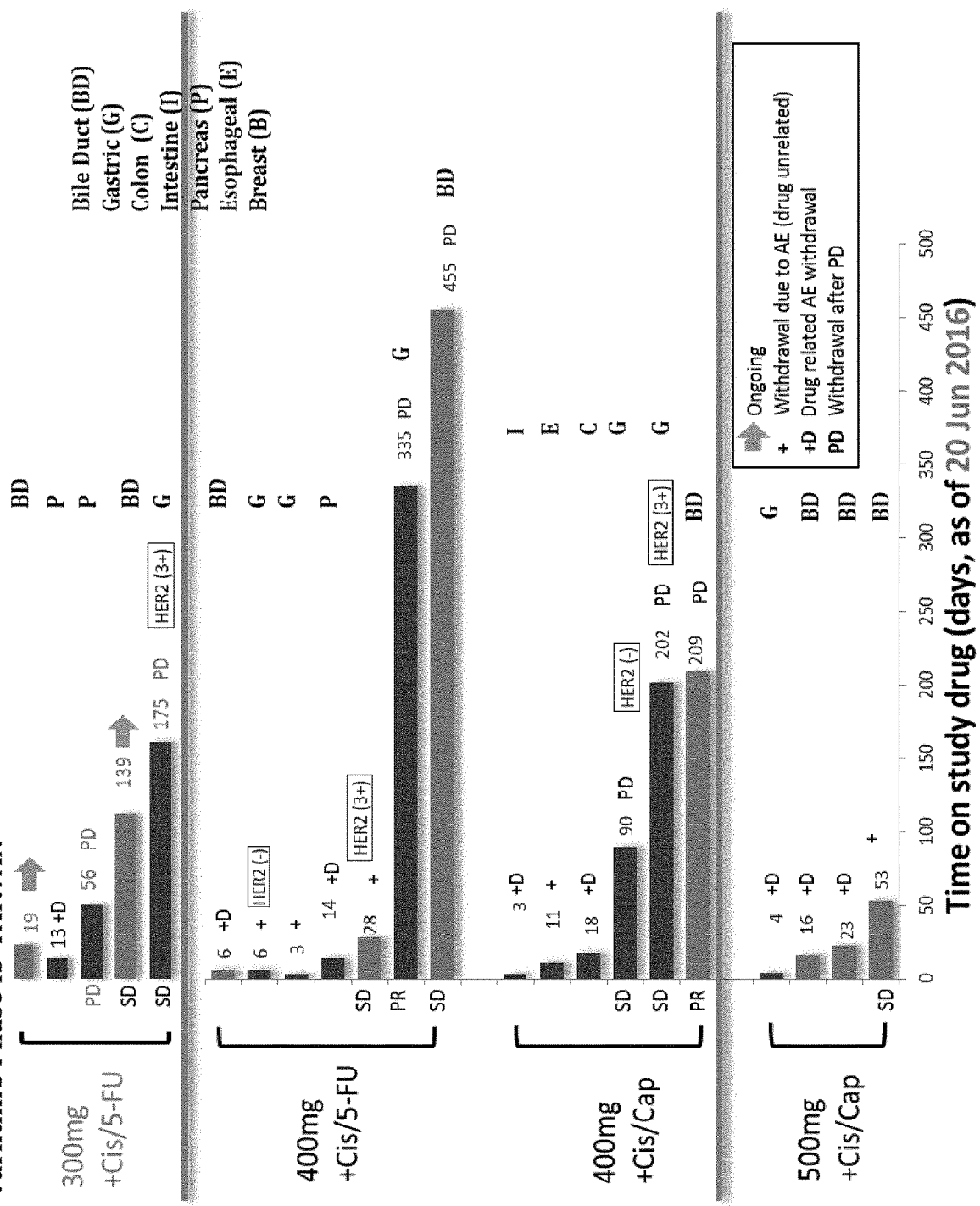
Figure 6a  Varlitinib Phase Ib-TAIWAN

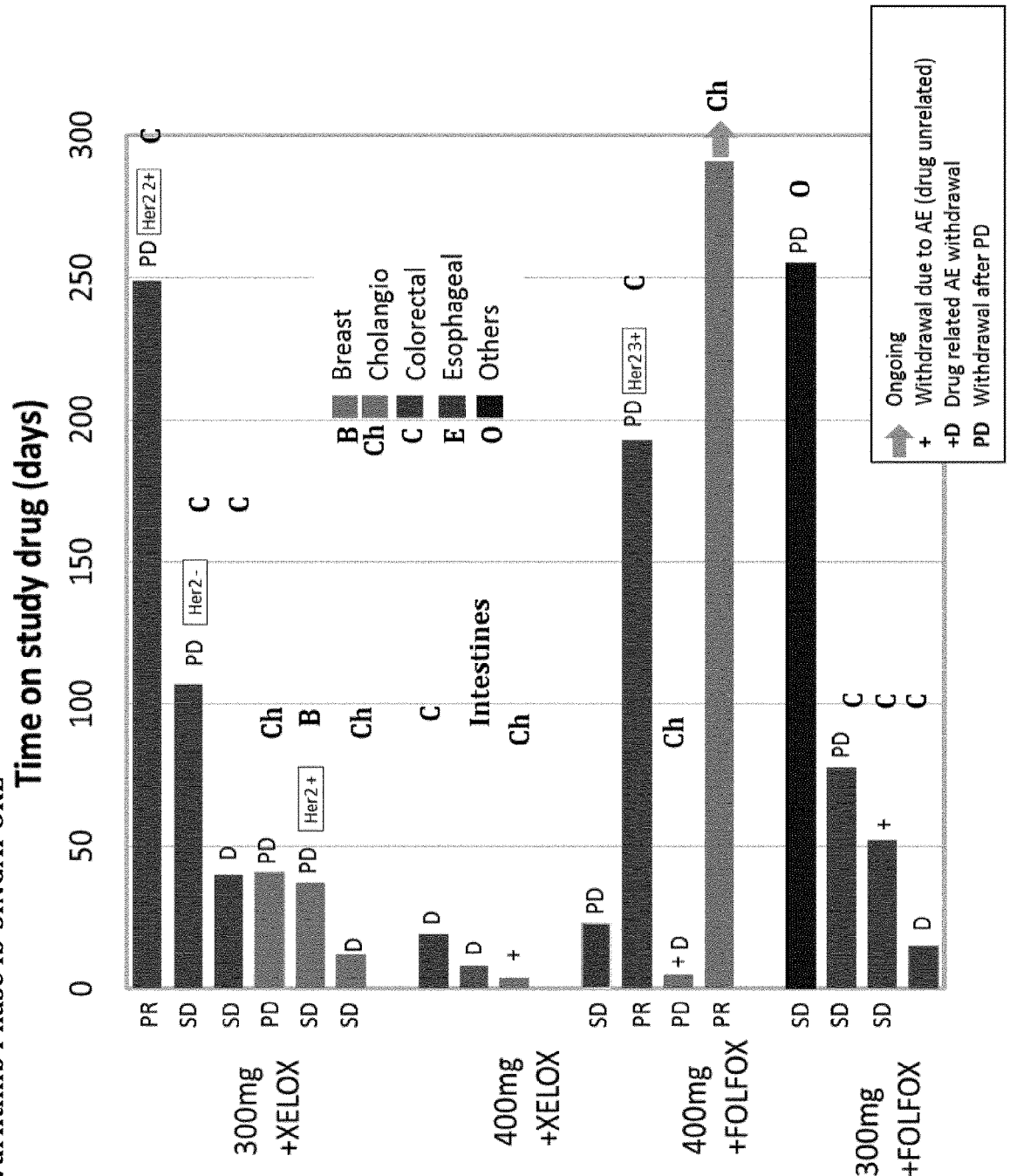
Figure 6b  Varlitinib Phase Ib-SINGAPORE

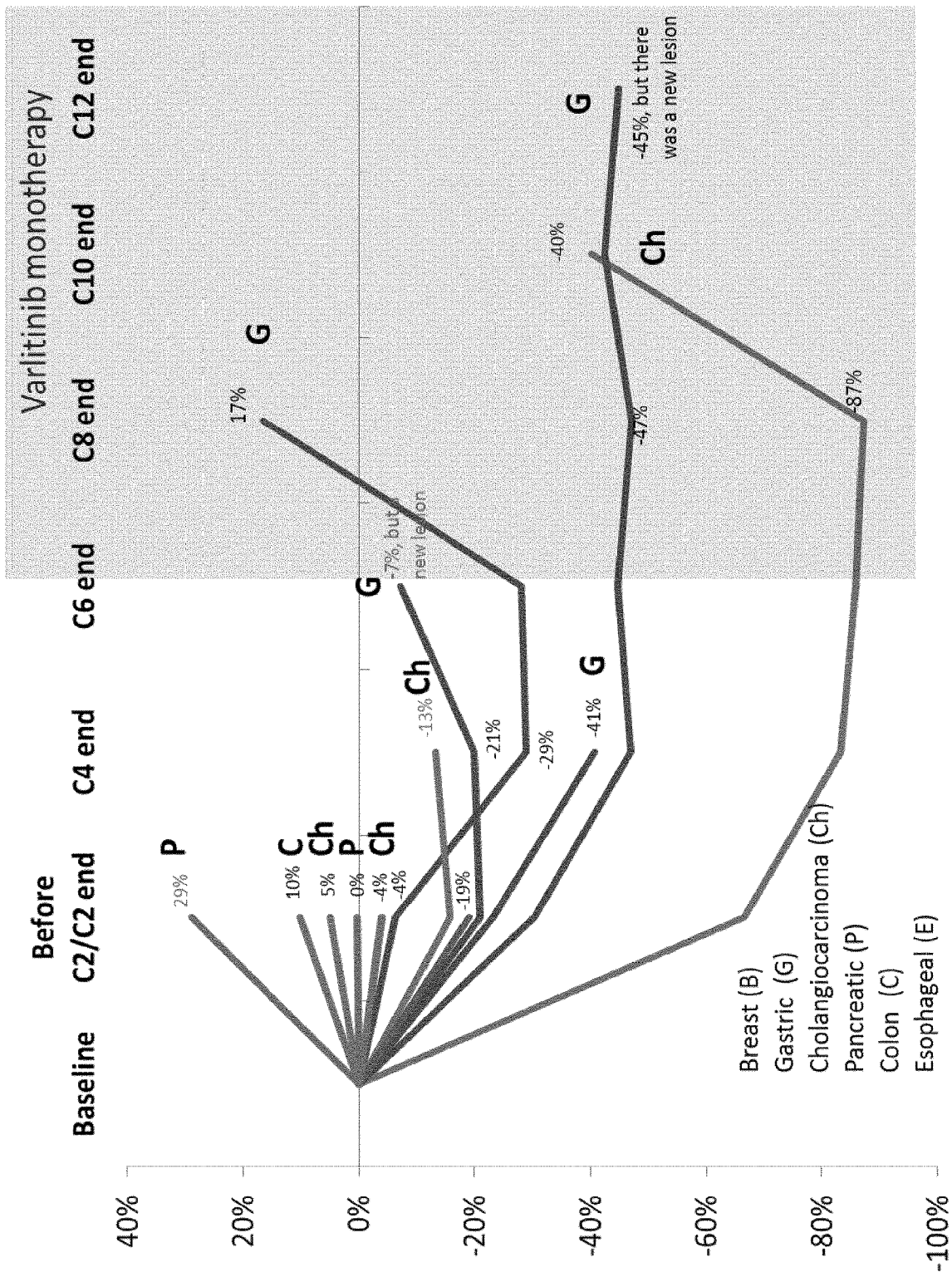
Figure 7a  Change in Target Lesion Over Time –TAIWAN (as of June 2016)

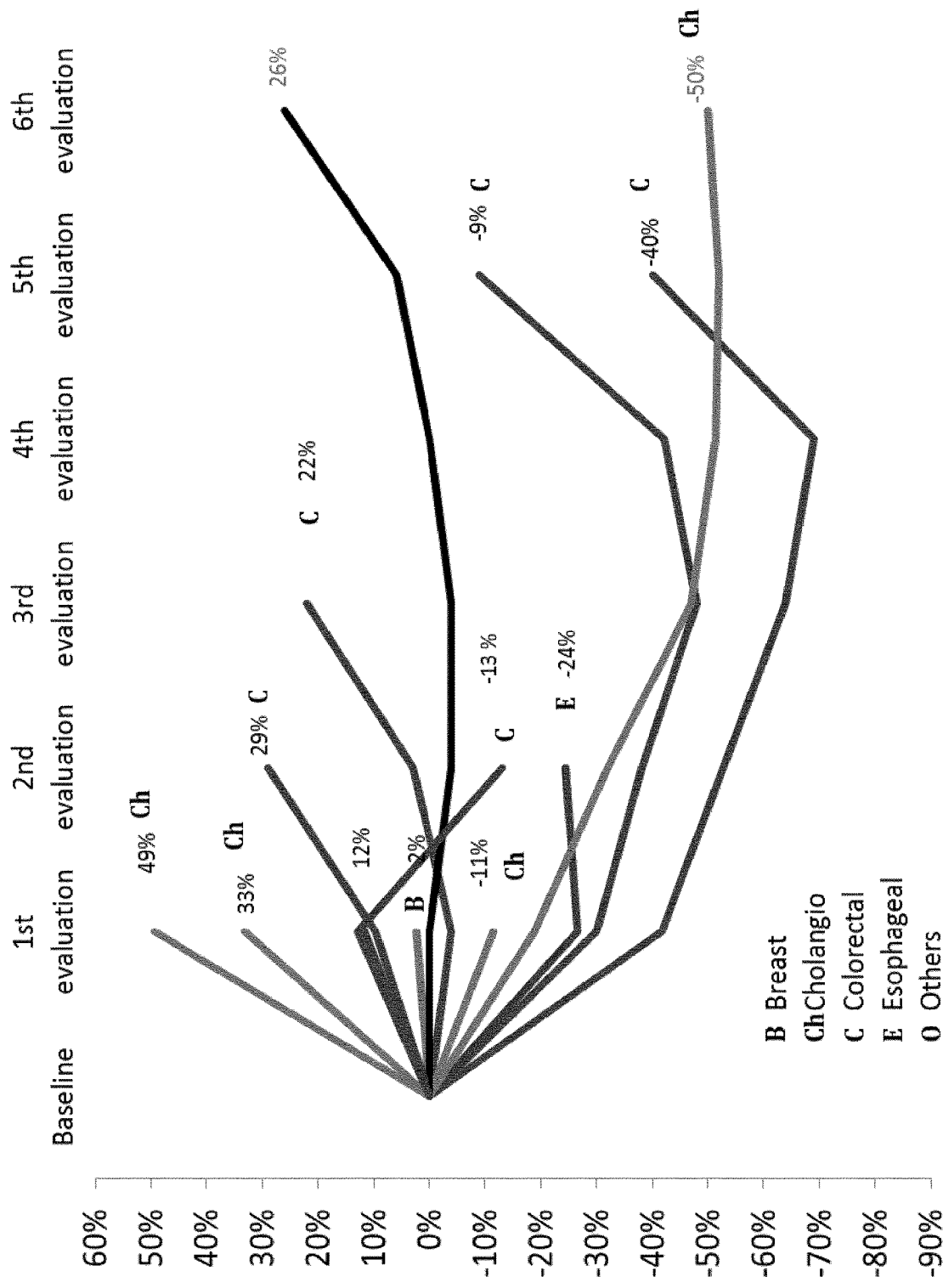
Figure 7b Change in Target Lesion Over Time – Phase Ib SINGAPORE

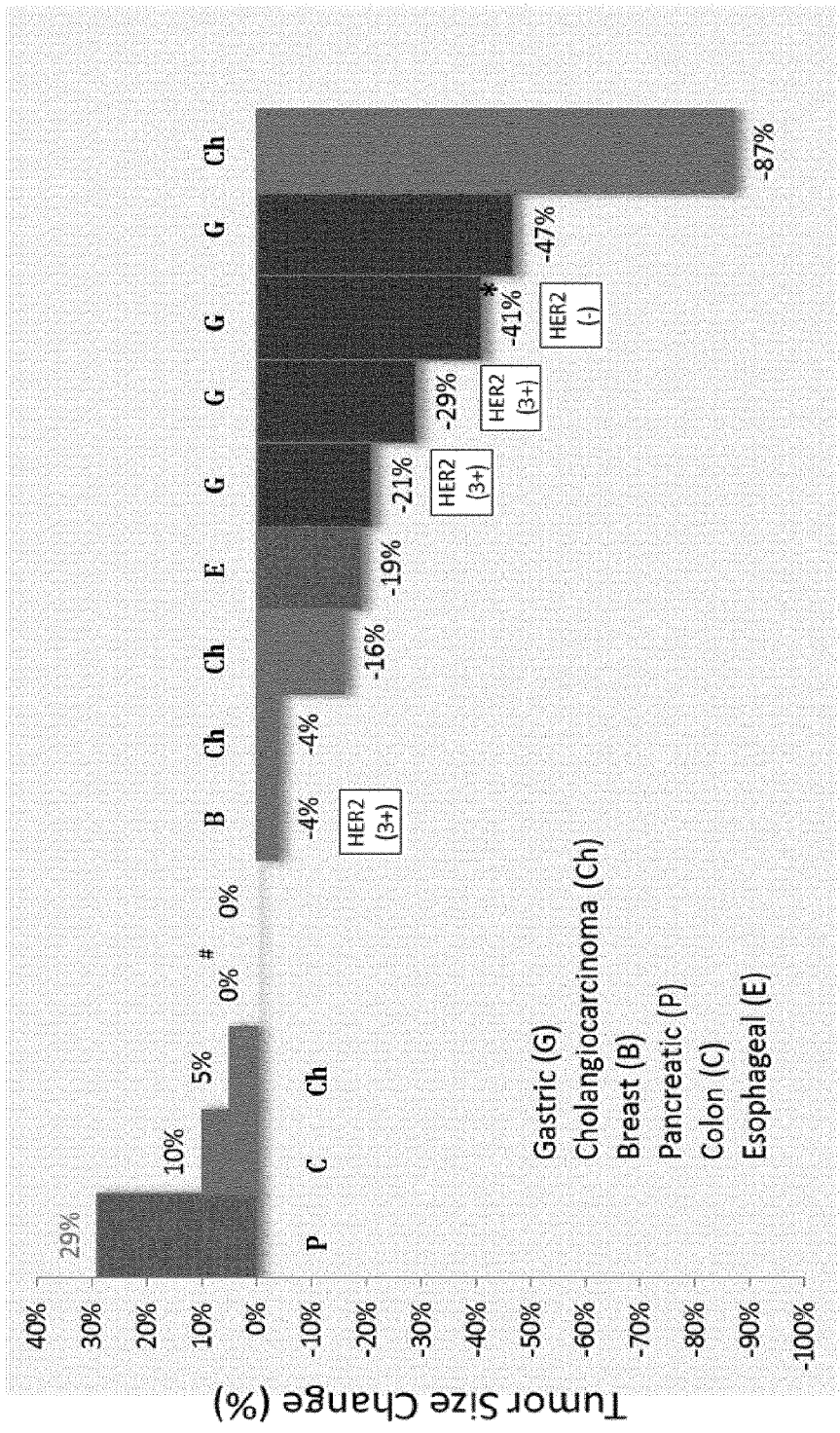
Figure 8a  Maximal % Change in Tumor Size from Baseline –TAIWAN (as of 20 June 2016)
- All patients received 300-500mg varlitinib and combined chemotherapy
2A101 is CCA without target lesion, and had best response as SD (non-measurable lesion)
*2B102-0001 has target lesion reduction to 41% at C4. However, new lesion developed, thus the overall RECIST response is PD.

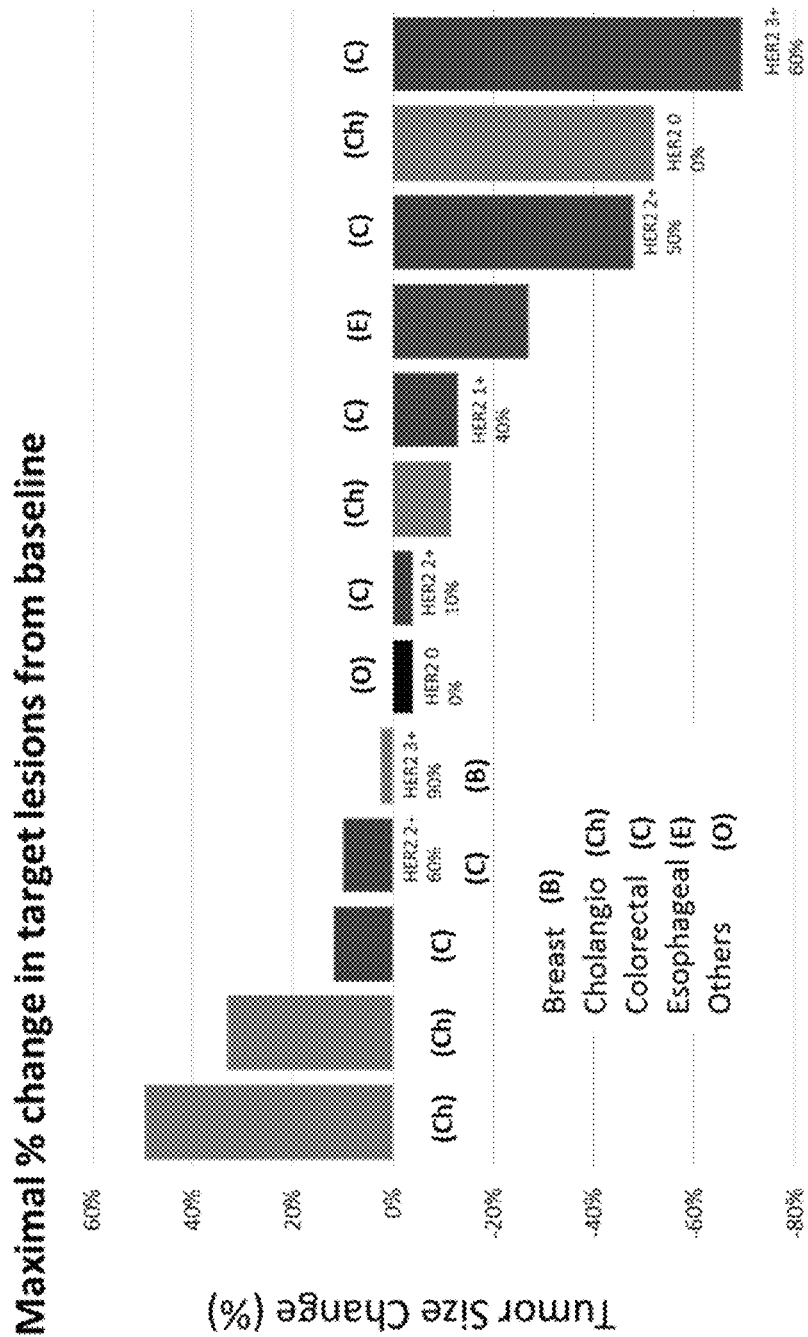
Figure 8b  Maximal % Change in Tumor Size from Baseline -SINGAPORE

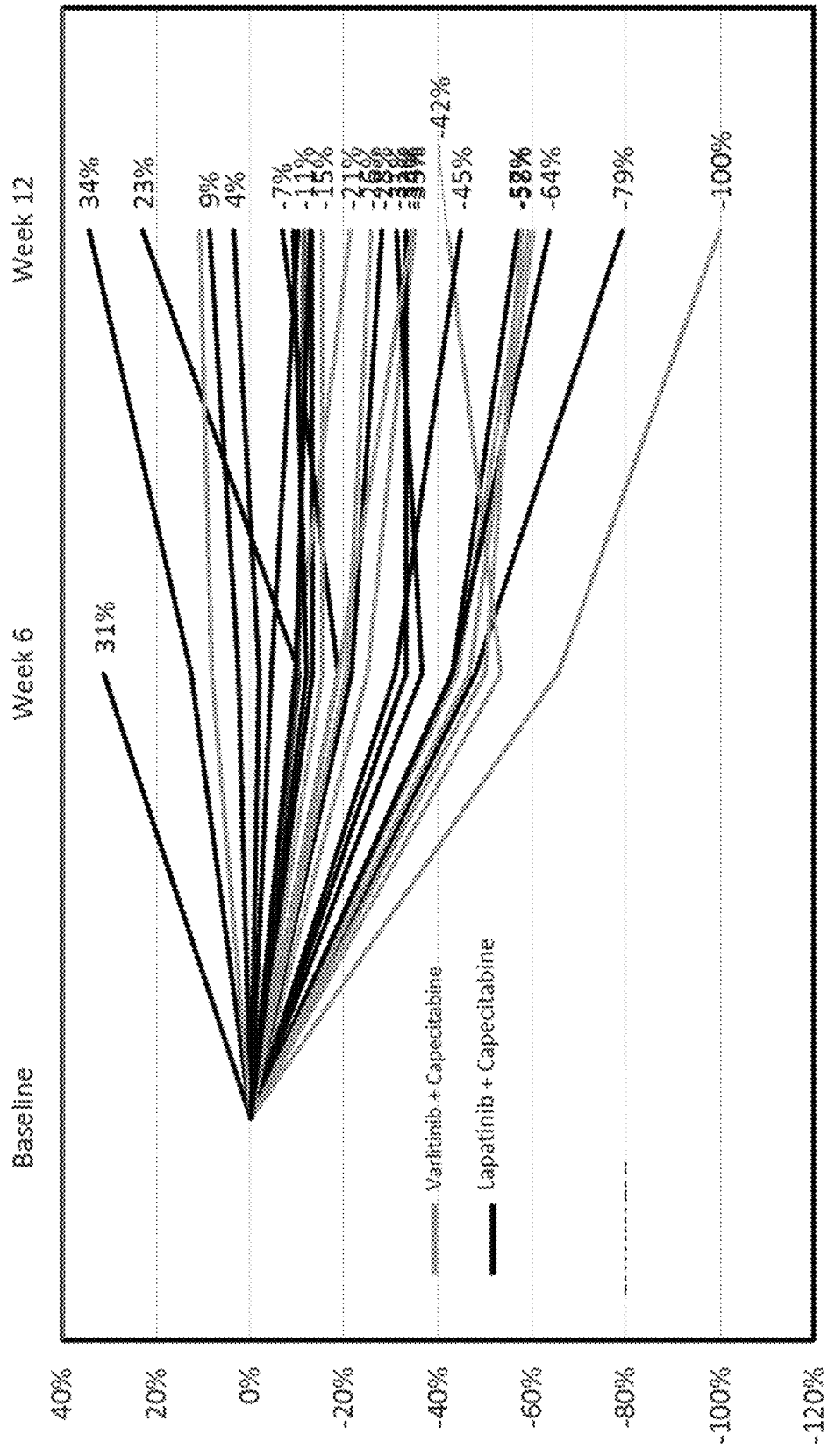

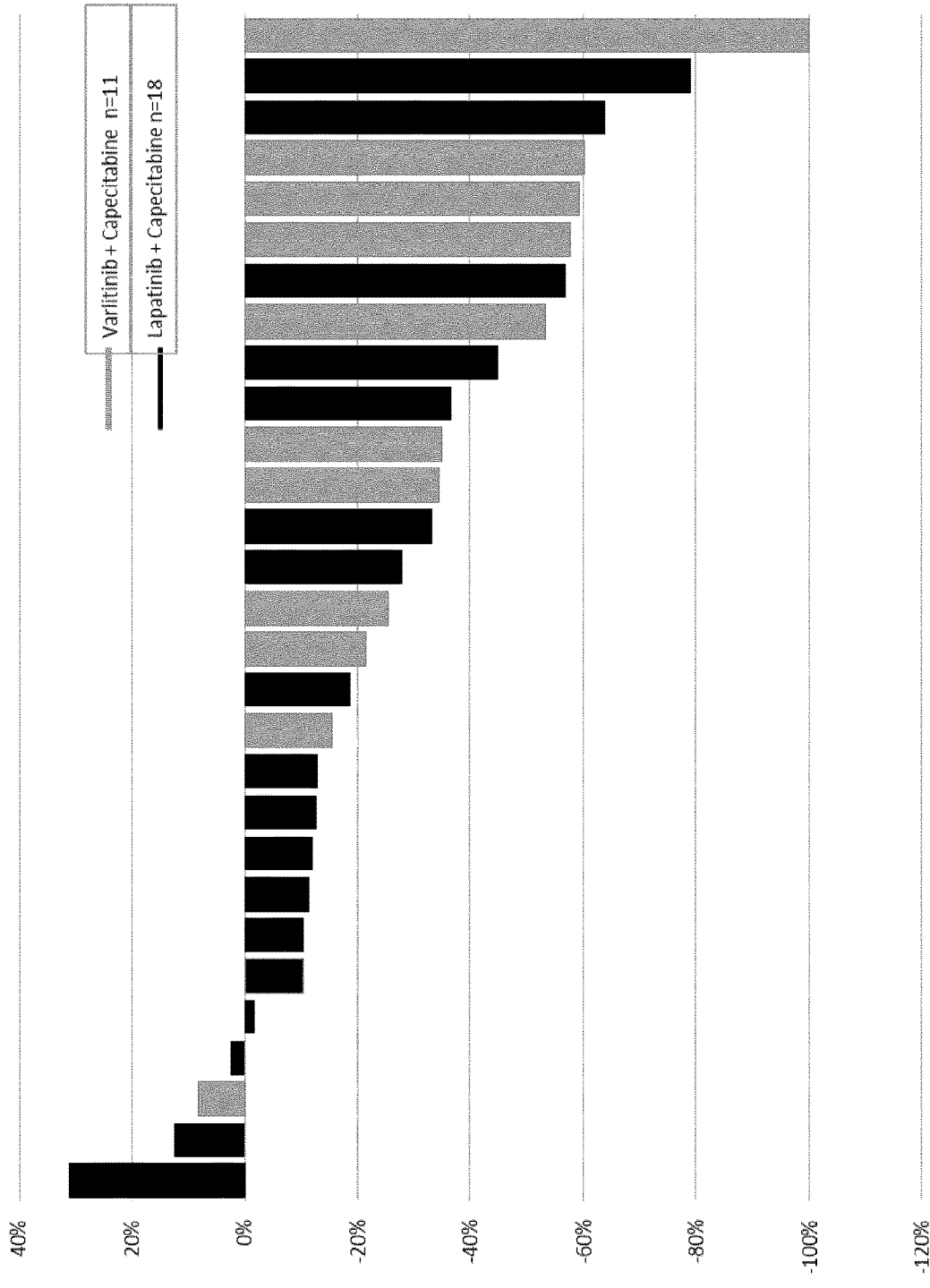
Figure 10 Phase 2A/B Breast Cancer Study with Varlitinib and Capecitabine or Lapatinib and Capecitabine- Waterfall Plot of Best Responses of Evaluable Subjects (RECIST % data, cut off date: 17 June 2016, n=29)

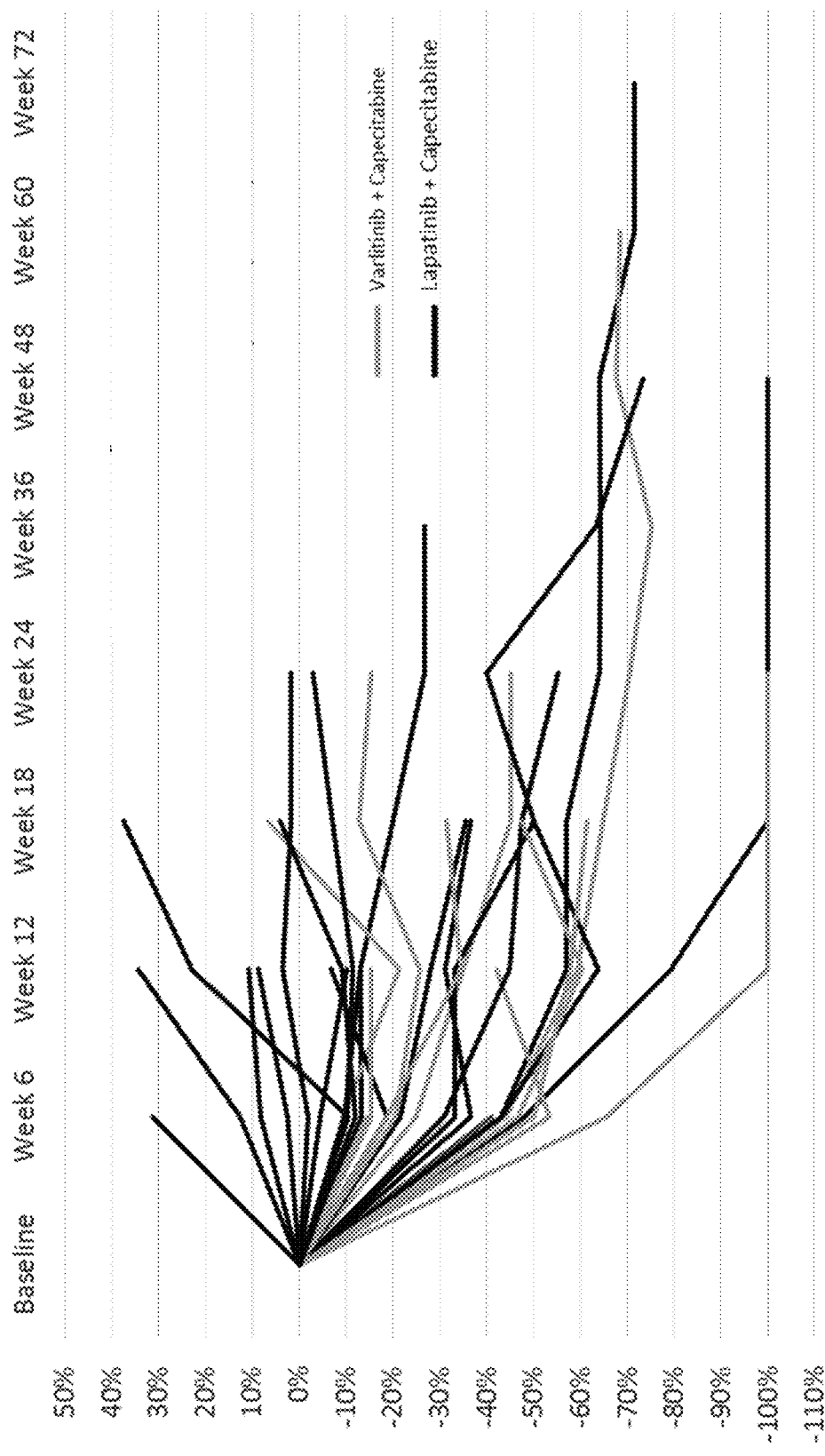
Figure 11 Phase 2A/B Breast Cancer Study with Varlitinib and Capecitabine or Lapatinib and Capecitabine- Best Responses All Subjects –Changes in Target Lesion Size Over Time

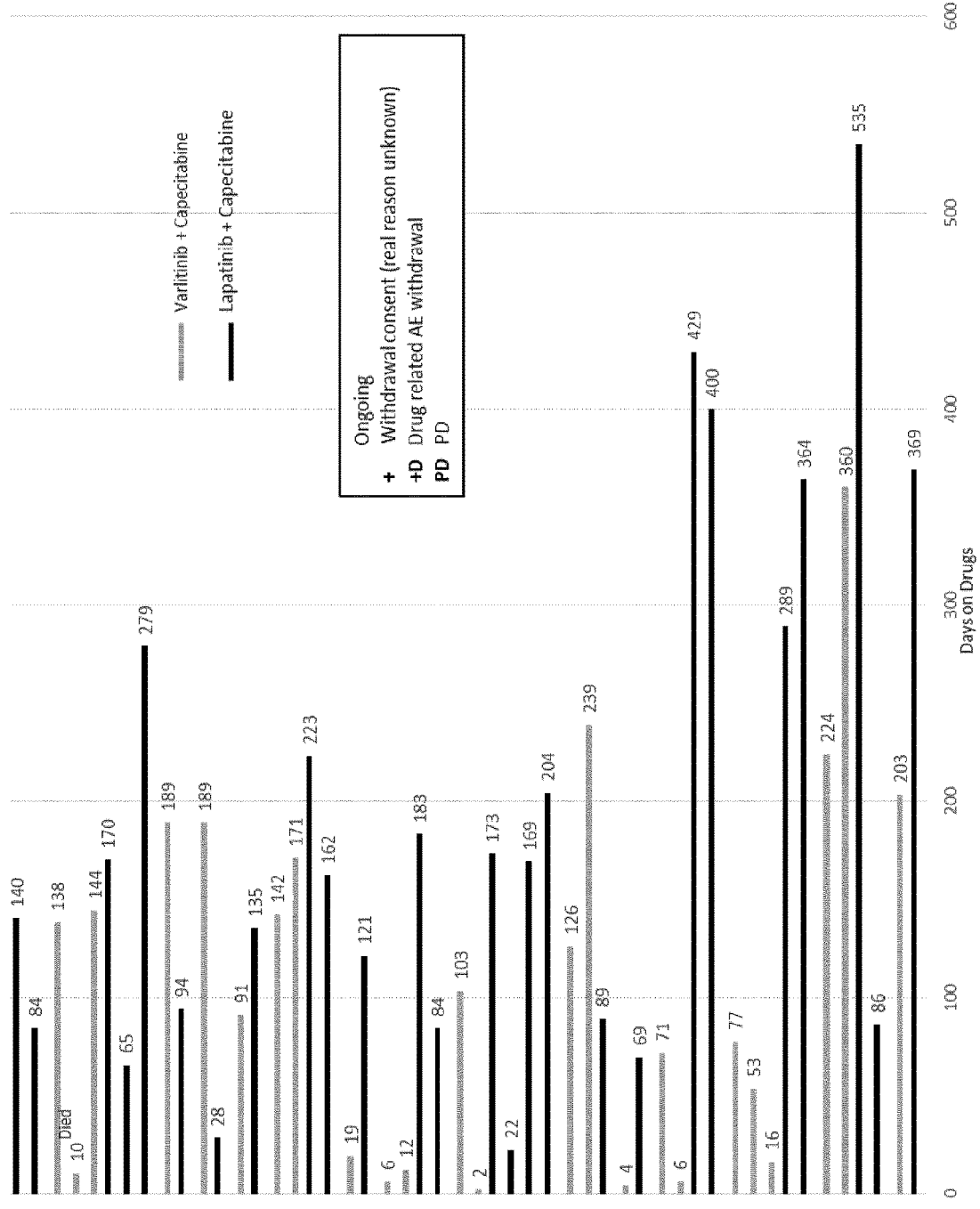
Figure 12 Days on Therapy (SINGAPORE)

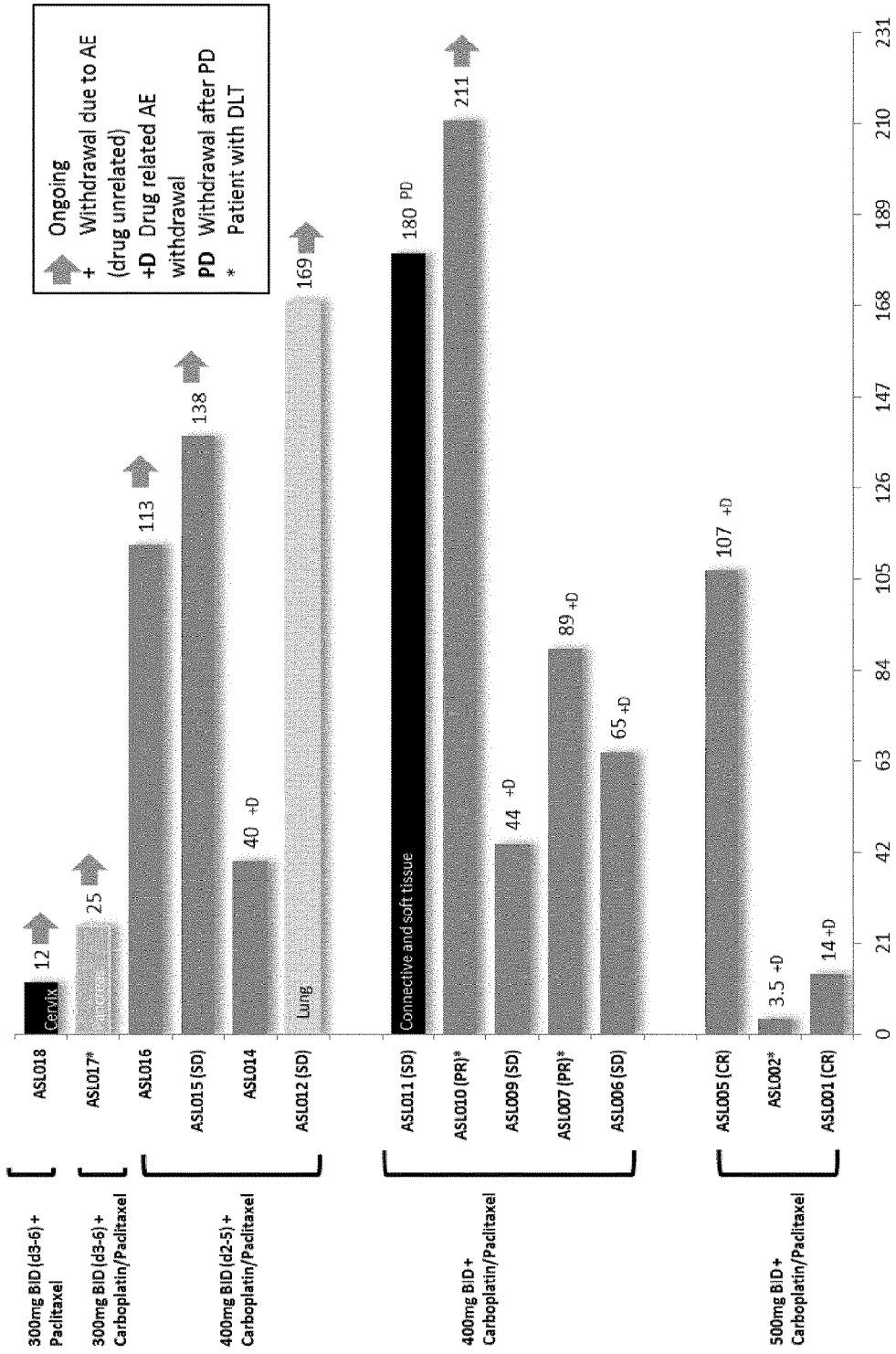

COMBINATION THERAPY COMPRISING VARLITINIB AND AN ANTICANCER AGENT

The present disclosure relates to a method of sensitizing a tumour and/or a metastasis/metastases in a cancer patient to chemotherapy, employing a type I tyrosine kinase inhibitor in combination with chemotherapy.

BACKGROUND

There are many cancers that are difficult to treat and although therapy is available, there appears to exist or to come into existence, a degree of resistance to the therapy. Primary resistance may occur in that cancer does not respond to treatment from the outset. This is may be due to the fact that the therapies used do not target precisely enough and effectively enough the type of cancer at hand. Secondary or acquired resistance also occurs quite frequently, which means that a therapy to which the patient seems to respond initially, at a certain time, loses its efficacy. With chemotherapy, for example overall approximately 80% of patients diagnosed with ovarian epithelial, primary peritoneal cancer will relapse after first-line platinum-based and taxane-based chemotherapy. That is not a very encouraging statistic.

There are numerous reasons for resistance, for example some cancers are discovered at a late stage and/or a simply not responsive to treatment.

Mechanisms by which cancers avoid the therapeutic effect of therapy include but are not limited to:
i) mutations which render the cancer less vulnerable to the treatment (e.g. mutation of the site of action of the therapy),
ii) active transportation of the drug out of the tumor, for example by p-glycolation,
iii) building up physical defences, for example stroma which inhibit certain immune responses, and
iv) certain cancers develop paths to repair damage caused by some anti-cancer therapies.

Tumor heterogeneity may also contribute to resistance, where small subpopulations of cells may acquire or stochastically already possess some of the features enabling them to emerge under selective drug pressure. This is a problem that many patients with cancer encounter, and it obviously limits the therapeutic alternatives that are effective and worsens the prognosis.

Cancer therapy guidelines describe recommended cancer therapies, which includes recommendations for the order or sequence in which the therapies are employed. Thus if a patients show disease progression on the first therapy ("first line"), then a next therapy ("second line") is recommended, and so on. These therapy recommendations are based on available scientific data and experience, and illustrate that resistance to one therapy does not exclude that another therapy may be effective. At a late stage cancers do not respond to most therapies and no more avenues of therapy exist. These cancers are completely therapy refractory, unless new therapies can be found which are effective.

Cholangiocarcinoma is a prime example of both primary and secondary resistance and is considered to be an incurable and a rapidly lethal malignancy unless both the primary tumor and any metastases can be fully resected (removed surgically). No curative treatment exists for cholangiocarcinoma except surgery. Unfortunately, most patients have advanced stage disease which is inoperable at the time of diagnosis. Patients with cholangiocarcinoma are generally managed—though never cured—with chemotherapy, radiation therapy, and other palliative care measures. These are also used as adjuvant therapies (i.e. post-surgically) in cases where resection has apparently been successful (or nearly so).

In the Western hemisphere cholangiocarcinoma is a relatively rare neoplasm that is classified as an adenocarcinoma (a cancer that forms glands or secretes significant amounts of mucins). It has an annual incidence rate of 1-2 cases per 100,000 in the Western world. However, rates of cholangiocarcinoma have been rising worldwide over the past several decades. Furthermore, the incidence is higher in Asian countries where it is recognized as a significant problem.

Thus there is a need for improved or alternative cancer therapies to address the unsolved problem of primary and secondary therapy resistance.

(R)—N4-[3-Chloro-4-(thiazol-2-ylmethoxy)-phenyl]-N6-(4-methyl-4,5,-dihydro-oxazol-2-yl)-quinazoline-4,6-diamine (Varlitinib Example 52 disclosed in WO2005/016346), is a small-molecule pan-HER inhibitor. It has been tested as a monotherapy in phase I clinical trials of gastric cancer patients. 23 patients, who had previously failed on one or more rounds of chemotherapy, and where eligible for trastuzumab, each received 500 mg of Varlitinib orally twice daily (BID) as monotherapy for 28 days. Tumour biopsies taken before and after treatment were analysed using immunohistochemistry. Signs of clinical activity included downregulation of signalling pathways responsible for cell proliferation, and a reduction in cell survival and cell proliferation in gastric tumours that were either co-expressing EGFR and HER2 or that were HER2 amplified.

Varlitinib has now been employed in combination with several different cytotoxic agents to treat cancer, after primary therapy has failed (either where the first line response became refractory, or wherein cancer did not respond to primary therapy). Some of the patients had previously received several lines of therapy, which had failed, until finally they were given Varlitinib in combination with chemotherapy.

The current experimental clinical data generated shows unexpected therapeutic activity of Varlitinib in particular in combination with cytotoxic agents. In some instances the patients had already received multiple rounds of different therapies including chemotherapy, which had all failed. Thus whilst Varlitinib has shown promising anticancer activity in its own right when Varlitinib is used in combination with chemotherapy, increased efficacy may be observed. This seems to be the case even when the patient was resistant to chemotherapy. Some of these patients show an encouraging "response" to the Varlitinib combination therapy. In several patients the therapy according to the present disclosure has shown a surprising level of efficacy.

The data generated suggests that Varlitinib used in combination with chemotherapy is a way to sensitize the cancer to treatment (either to Varlitinib or to the chemotherapy or both), in particular to treatment with cytotoxic chemotherapy.

SUMMARY OF THE DISCLOSURE

Thus there is provided a method of treating a cancer patient by:
a) administering a therapeutically effective amount of a compound of formula (I):

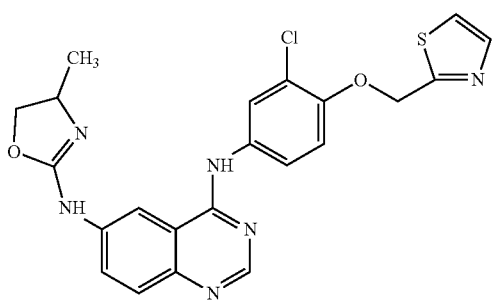 [SMILES: CC1COC(Nc2ccc3ncnc(Nc4ccc(OCc5nccs5)c(Cl)c4)c3c2)=N1]

an enantiomer thereof or a pharmaceutically acceptable salt of any one of the same, and b) administering a further cancer therapy.

In one independent aspect there is provided a method of sensitizing a cancer patient to chemotherapy by:

a) administering a therapeutically effective amount of a compound of formula (I):

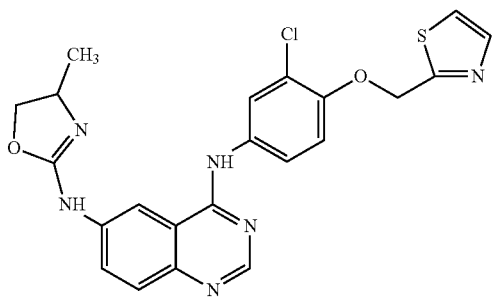 [SMILES: CC1COC(Nc2ccc3ncnc(Nc4ccc(OCc5nccs5)c(Cl)c4)c3c2)=N1]

an enantiomer thereof or a pharmaceutically acceptable salt of any one of the same, and b) administering a chemotherapeutic agent or a combination of chemotherapeutic agents, for example wherein the pharmacology effect of the compound of formula (I) and the chemotherapy overlap in the patient.

Thus in one aspect there is provided use of a compound of formula (I) as defined herein in treatment to sensitize a cancer patient to chemotherapy.

Thus in one embodiment there is provided a compound of formula (I) and a chemotherapeutic agent (in particular a cytotoxic chemotherapeutic agent) for use in treatment of cancer, in particular refractory or resistant cancer.

In one aspect there is provided use of a compound of formula (I) for the manufacture of a medicament for sensitizing a cancer patient to chemotherapy.

In one aspect there is provided use of a compound of formula (I) and a chemotherapeutic agent (in particular a cytotoxic chemotherapeutic agent) for the manufacture of a medicament for treating cancer, in particular refractory cancer.

In one embodiment the patient population are refractory and/or resistant to chemotherapy, for example refractory. In one embodiment the patient population is resistant.

The present inventors have treated a number of very sick cancer patients including some who were refractory or resistant to a whole host of treatments, including new experimental medicines. Surprisingly the patients treated have responded to chemotherapy when they have been administered Valitinib, for example one 78 year-old male with Her2 positive (3+) stage IV gastric cancer had progressive disease following:

first line treatment with cisplatin and Xeloda® (capecitabine)—4 cycles, second line treatment with the experimental drug TDM1 (an antibody drug conjugate comprising Herceptin® now named ado-trastuzumab emtansine)—9 cycles, third line treatment with experimental drug LJM716 (a HER3 monoclonal antibody) and Herceptin®.

After treatment cycle 4 with Varlitinib 400 mg bi-daily, cisplatin and capecitabine the patient showed a 29% response and was categorised as having stable disease.

A 46 year-old female with gastric cancer given first line treatment of Varlitinib 400 mg bi-daily, cisplatin and capecitabine showed a 41% response after cycle 4.

A 56 year-old male with stage IV cholangiocarcinoma had progressive disease following treatment with:

radiotherapy, and gemcitabine (Gemzar®) and cisplatin-6 months.

After treatment cycle 6 with Varlitinib 400 mg bi-daily, cisplatin and capecitabine the patient showed an 85.77% response. This patient can be considered to be a super-responder based on these extraordinary results.

In the Example section discloses more details for these patients and details for patients of treatment of other patients with a combination therapy according to the present disclosure. The results look extremely exciting because improvement, sometime dramatic improvement is seen in the very sick-patients some of whom their cancers were effectively untreatable.

In one embodiment the compound of formula (I) is (R)—N4-[3-Chloro-4-(thiazol-2-ylmethoxy)-phenyl]-N6-(4-methyl-4,5,-dihydro-oxazol-2-yl)-quinazoline-4,6-diamine (Varlitinib):

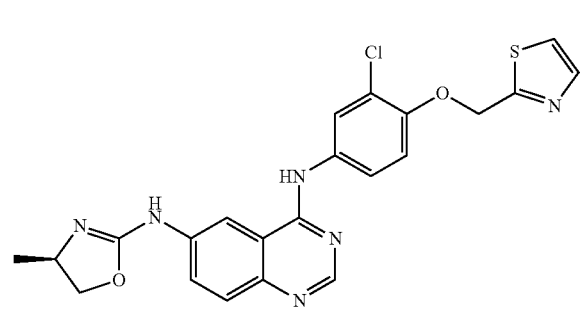 [SMILES: C[C@@H]1COC(Nc2ccc3ncnc(Nc4ccc(OCc5nccs5)c(Cl)c4)c3c2)=N1]

or a pharmaceutically acceptable salt thereof or a pro-drug thereof.

In one embodiment the compound of formula (I), such as Varlitinib, is employed in combination with a further HER inhibitor, for example a combination of a compound of formula (I) (such as Varlitinib) and Herceptin (trastuzumab) and/or pertuzumab. Surprisingly a combination of Varlitinib and Herceptin show more therapeutic activity than either entity alone.

In one embodiment the combination of ado-trastuzumab-emtansine and a compound of formula (I), such as Varlitinib.

These combinations of HER inhibitor therapy may be employed with a chemotherapy agent according to the present disclosure.

The disclosure also extends to administration of a pharmaceutical formulation comprising any one of the same and excipient, diluent or carrier.

Varlitinib at an appropriate dose is capable of inhibiting HER1, HER2 and HER4 directly and thought to be capable of inhibiting HER3 indirectly.

In one embodiment the compound of formula (I), such as Varlitinib, at least inhibits the activity of HER1 and HER2, HER1 and HER4 or HER2 and HER4.

In one embodiment the compound of formula (I), such as Varlitinib, at least inhibits the activity of HER1, HER2 and HER4, for example directly inhibits the activity of HER1, HER2 and HER4.

In one embodiment the compound of formula (I), such as Varlitinib, inhibits the activity of HER1, HER2, HER3 and HER4, for example directly inhibits the activity of HER1, HER2, and HER4, and indirectly inhibits the activity of HER3.

In one embodiment the compound of formula (I), such as Varlitinib, is administered orally.

In one embodiment each dose of the compound of formula (I), such as Varlitinib, is in the range 100 to 900 mg, for example each dose is in the range of 300 to 500 mg, such as 400 mg, for example administered once or twice daily, such as twice daily.

In one embodiment the compound of formula (I), such as Varlitinib, is administered in a 28 days treatment cycle.

In one embodiment the target patient population is EGFR and HER2 positive or are HER2 amplified.

In one embodiment the treatment of the present disclosure is administered for a non-epithelial cancer in which HER inhibition is effective.

In one embodiment the treatment of the present disclosure is administered for epithelial cancer, for example is selected from liver cancer (such as hepatocellular carcinoma), biliary tract cancer, breast cancer (such as none ER+ breast cancer), prostate cancer, colorectal cancer, ovarian cancer, cervical cancer, lung cancer, gastric cancer, pancreatic, bone cancer, bladder cancer, head and neck cancer, thyroid cancer, skin cancer, renal cancer, and oesophagus cancer, for example gastric cancer.

In one embodiment the cancer is selected from selected from the group comprising hepatocellular carcinoma, cholangiocarcinoma, breast cancer, prostate cancer, colorecetal cancer, ovarian cancer, lung cancer, gastric cancer, pancreatic and oesophagus cancer.

In one embodiment the biliary duct cancer is in a location selected from intrahepatic bile ducts, left hepatic duct, right hepatic duct, common hepatic duct, cystic duct, common bile duct, Ampulla of Vater and combinations thereof.

In one embodiment the biliary duct cancer is in an intrahepatic bile duct.

In one embodiment the biliary duct cancer is in a left hepatic duct.

In one embodiment the biliary duct cancer is in a right hepatic duct.

In one embodiment the biliary duct cancer is in a common hepatic duct

In one embodiment the biliary duct cancer is in a cystic duct.

In one embodiment the biliary duct cancer is in a common bile duct.

In one embodiment the biliary duct cancer is in an Ampulla of Vater.

In one embodiment the epithelial cancer is a carcinoma.

In one embodiment the combination treatment according to the disclosure is adjuvant therapy, for example after surgery.

In one embodiment the combination therapy according to the disclosure is neoadjuvant treatment, for example to shrink a tumour before surgery.

In one embodiment the tumour is a solid tumour. In one embodiment the cancer is a primary cancer, secondary cancer, metastasis or combination thereof. In one embodiment the treatment according to the present disclosure is suitable for the treatment of secondary tumours. In one embodiment the cancer is metastatic cancer. In one embodiment the treatment according to the present disclosure is suitable for the treatment of primary cancer and metastases. In one embodiment the treatment according to the present disclosure is suitable for the treatment of secondary cancer and metastases. In one embodiment the treatment according to the present disclosure is suitable for the treatment of primary cancer, secondary cancer and metastases.

In one embodiment the treatment according to the present disclosure is suitable for the treatment of cancerous cells in a lymph node, for a cancer of the present disclosure.

In one embodiment the liver cancer is primary liver cancer. In one embodiment the liver cancer is secondary liver cancer. In one embodiment the liver cancer is stage 1, 2, 3A, 3B, 3C, 4A or 4B.

In one embodiment the gastric cancer is stage 0, I, II, III or IV.

In one embodiment Varlitinib is continued as a monotherapy after the combination therapy of the present disclosure, for example administered once or twice daily at a dose in the range 100 mg to 500 mg, such as 200 mg, 300 mg or 400 mg.

In one embodiment the monotherapy is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 months or more.

In one embodiment the patient is a human.

DETAILED DISCLOSURE

Varlitinib has significant anticancer activity when employed as a monotherapy. However, increased efficacy is observed with Varlitinib is employed in combination therapy, in particular with chemotherapy, even when the patient did not respond to chemotherapy in the absence of Varlitinib. Whilst not wishing to be bound by theory the administration of Varlitinib seems to restore at least some of the therapeutic activity of the chemotherapy, in resistant or refractory patients.

Thus sensitization to chemotherapy as employed herein simply refers to the fact a combination of the compound of formula (I) in combination with a chemotherapy has increased efficacy in comparison to one or both therapies employed alone. The sensitization treatment according to the present disclosure can be employed in patients who have primarily resistant to treatment, such as chemotherapy. The sensitization treatment according to the present disclosure can be employed in patients who have secondary resistant to treatment, such as chemotherapy. The sensitization treatment according to the present disclosure can be employed in patients who have not shown resistance, in an attempt to avoid them becoming resistant.

Thus in one embodiment sensitizing a cancer patient to chemotherapy as employed herein refers to rendering the cancer cells more susceptible to the therapeutic/killing effects of chemotherapy and/or to the compound of formula (I) such as Varlitinib, or reciprocally to both therapies, in comparison to the "same" cancer cells without treatment with a compound of formula (I).

To obtain the benefits of sensitization to chemotherapy then the chemotherapy has to administered in a time frame, where the pharmacological effects of a compound of formula (I) and the chemotherapy overlap, i.e. the treatment regimens for the said therapies partly coincide in time A skilled person will understand in practice what this means.

"Administering a combination therapy" as employed herein does not require the therapies employed in the combination to be administered at the same time.

Combination therapy as employed herein refers to two or more modes of therapy being employing over the same treatment period, i.e. the opposite of sequential therapy.

Two or more modes of therapy as employed herein refers to at least two therapies which have different modes of action and/or different activities and/or different routes of administration.

Unless the context indicated otherwise refractory and resistant are used to interchangeably herein to refer to where the cancer does not respond to therapy or does not responds poorly to therapy.

In some instances patients may benefit from having the initial dose reduced to 300 mg or 200 mg bi-daily.

Other patients may benefit from receiving the compound of formula (I), such as Varlitinib for in a regime which is non-continuous, for example taking medication on alternate days instead of each day or taking medication for four sequential days followed by one, two or three days without medication.

In one embodiment the compound of formula (I) is administered as pharmaceutical formulation comprising one or more pharmaceutically acceptable excipients. In one embodiment the compound of formula (I) is administered orally, for example as tablet or capsule.

In one embodiment the treatment regime for the compound of formula (I) is commenced before chemotherapy is commenced and is continued until at least the chemotherapy is started, in particular is continued for at least the duration of the chemotherapy.

In one embodiment the treatment regime for the compound of formula (I) is commenced concomitantly with the commencement of the chemotherapy and continued for at least the duration of the chemotherapy.

Thus in one embodiment the compound of formula (I) and the chemotherapy are administered on the same day.

Thus the pharmacology effect of the compound of formula (I) and the chemotherapy overlap in the patient when the effects of the compound of formula (I) can render the cancer cells in more susceptible to chemotherapy than they would be otherwise.

In one embodiment the chemotherapy is cytotoxic chemotherapy.

In one embodiment the combination therapy according to the present disclosure comprises a RON inhibitor, for example as disclosed WO2008/058229, incorporated herein by reference.

In one embodiment the combination therapy comprises a checkpoint inhibitor, such as a CTLA4 inhibitor, a PD-1 inhibitor or a PD-L1 inhibitor, in particular an antibody or binding fragment thereof.

Examples of pharmaceutically acceptable salts include but are not limited to acid addition salts of strong mineral acids such as HCl and HBr salts and addition salts of strong organic acids, such as a methansulfonic acid salt, tosylates, furoates and the like, including di, tri salts thereof, such as ditosylates.

Analytical tests for assessing the expression or over expression of HER2 are known and available in the art.

Cancers

Liver cancer as employed herein refers to cancer of the liver, for example hepatocellular carcinoma including fibrolamellar carcinoma, cholangiocarcinoma, angiosarcoma and hepatoblastoma.

Gastric cancer as employed herein refers to cancer of the stomach, for example squamous cell cancers, lymphoma including non-hodgkin lymphoma, gastrointestinal stromal tumour, or neuroendocrine tumours.

Prostate cancer as employed herein refers to cancer of the prostate, for example ductal adenocarcinoma, transitional cell (urothelial cancer), squamous cell cancer, carcinoid of the prostate, small cell cancer or sarcoma and sarcomatoid cancer.

Pancreatic cancer as employed herein includes exocrine cancers (including rare forms thereof such as cystic tumours, and cancer of the acinar cells), endocrine pancreatic tumours (including gastrinomas, insulinomas, somatostatinomas, VIPomas, glucagonomas), pancreatoblastoma, sarcomas of the pancreas and lymphoma.

Biliary tract cancer as employed herein refers to cholangiocarcinoma (intrahepatic, extrahepatic), gall bladder cancer and ampullary carcinoma.

Colorectal cancer as employed herein refers to cancer or the colon and/or rectum and includes squamous cell cancers, carcinoid tumours, sarcomas and lymphomas.

Breast cancer as employed herein refers to cancer of the breast and includes ductal cardinoma in situ, lobular carcinoma in situ, invasive ductal breast cancer, invasive lobular breast cancer, invasive breast cancer, Paget's disease, angiosarcoma of the breast and rare types of breast cancer such as medullary breast cancer, mucinous breast cancer, tubular breast cancer, adenoid cystic carcinoma of the breast metaplastic breast cancer, basal type breast cancer and papillary breast cancer.

Ovarian cancer as employed herein refers to cancer of an ovary and includes serious, endometrioid, clear cell, mucinous, undifferentiated or unclassified, germline and other rare ovarian tumours such as teratoma of the ovary (mature teratoma and immature teratoma) and borderline ovarian tumours. Epithelia ovarian cancers are serious, endometrioid, clear cell, mucinous and undifferentiated or unclassified.

There are more than 30 different types of ovarian cancer which are classified according to the type of cell from which they start Cancerous ovarian tumours can start from three common cell types:
  Surface Epithelium—cells covering the lining of the ovaries
  Germ Cells—cells that are destined to form eggs
  Stromal Cells—Cells that release hormones and connect the different structures of the ovaries The present disclosure relates to treatment of ovarian cancer from any source, for example as described herein, in particular epithelium cells. Epithelial ovarian carcinomas (EOCs) account for 85 to 90 percent of all cancers of the ovaries.

Common Epithelial Tumours—

Epithelial ovarian tumours develop from the cells that cover the outer surface of the ovary. Most epithelial ovarian tumours are benign (noncancerous). There are several types of benign epithelial tumours, including serous adenomas, mucinous adenomas, and Brenner tumours. Cancerous epithelial tumours are carcinomas—meaning they begin in the tissue that lines the ovaries. These are the most common and most dangerous of all types of ovarian cancers. Unfortunately, almost 70 percent of women with the common epithelial ovarian cancer are not diagnosed until the disease is advanced in stage.

There are some ovarian epithelial tumours whose appearance under the microscope does not clearly identify them as cancerous. These are called borderline tumours or tumours of low malignant potential (LMP tumours). The method of the present disclosure includes treatment of the latter.

Germ Cell Tumours—

Ovarian germ cell tumours develop from the cells that produce the ova or eggs. Most germ cell tumours are benign (non-cancerous), although some are cancerous and may be life threatening. The most common germ cell malignancies are maturing teratomas, dysgerminomas, and endodermal sinus tumours. Germ cell malignancies occur most often in teenagers and women in their twenties. Today, 90 percent of patients with ovarian germ cell malignancies can be cured and their fertility preserved.

Stromal Tumours—

Ovarian stromal tumours are a rare class of tumours that develop from connective tissue cells that hold the ovary together and those that produce the female hormones, estrogen and progesterone. The most common types are granulosa-theca tumours and Sertoli-Leydig cell tumours. These tumours are quite rare and are usually considered low-grade cancers, with approximately 70 percent presenting as Stage I disease (cancer is limited to one or both ovaries).

Primary Peritoneal Carcinoma—

The removal of one's ovaries eliminates the risk for ovarian cancer, but not the risk for a less common cancer called Primary Peritoneal Carcinoma. Primary Peritoneal Carcinoma is closely rated to epithelial ovarian cancer (most common type). It develops in cells from the peritoneum (abdominal lining) and looks the same under a microscope. It is similar in symptoms, spread and treatment.

Stages of Ovarian Cancer

Once diagnosed with ovarian cancer, the stage of a tumour can be determined during surgery, when the doctor can tell if the cancer has spread outside the ovaries. There are four stages of ovarian cancer—Stage I (early disease) to Stage IV (advanced disease). The treatment plan and prognosis (the probable course and outcome of your disease) will be determined by the stage of cancer you have.

Following is a description of the various stages of ovarian cancer:

Stage I—Growth of the cancer is limited to the ovary or ovaries.

Stage IA—Growth is limited to one ovary and the tumour is confined to the inside of the ovary. There is no cancer on the outer surface of the ovary. There are no ascites present containing malignant cells. The capsule is intact.

Stage IB—Growth is limited to both ovaries without any tumour on their outer surfaces. There are no ascites present containing malignant cells. The capsule is intact.

Stage IC—The tumour is classified as either Stage IA or IB and one or more of the following are present: (1) tumour is present on the outer surface of one or both ovaries; (2) the capsule has ruptured; and (3) there are ascites containing malignant cells or with positive peritoneal washings.

Stage II—Growth of the cancer involves one or both ovaries with pelvic extension.

Stage IIA—The cancer has extended to and/or involves the uterus or the fallopian tubes, or both.

Stage IIB—The cancer has extended to other pelvic organs.

Stage IIC—The tumour is classified as either Stage IIA or IIB and one or more of the following are present: (1) tumour is present on the outer surface of one or both ovaries; (2) the capsule has ruptured; and (3) there are ascites containing malignant cells or with positive peritoneal washings.

Stage III—Growth of the cancer involves one or both ovaries, and one or both of the following are present: (1) the cancer has spread beyond the pelvis to the lining of the abdomen; and (2) the cancer has spread to lymph nodes. The tumour is limited to the true pelvis but with histologically proven malignant extension to the small bowel or omentum.

Stage IIIA—During the staging operation, the practitioner can see cancer involving one or both of the ovaries, but no cancer is grossly visible in the abdomen and it has not spread to lymph nodes. However, when biopsies are checked under a microscope, very small deposits of cancer are found in the abdominal peritoneal surfaces.

Stage IIIB—The tumour is in one or both ovaries, and deposits of cancer are present in the abdomen that are large enough for the surgeon to see but not exceeding 2 cm in diameter. The cancer has not spread to the lymph nodes.

Stage IIIC—The tumour is in one or both ovaries, and one or both of the following is present: (1) the cancer has spread to lymph nodes; and/or (2) the deposits of cancer exceed 2 cm in diameter and are found in the abdomen.

Stage IV—This is the most advanced stage of ovarian cancer. Growth of the cancer involves one or both ovaries and distant metastases (spread of the cancer to organs located outside of the peritoneal cavity) have occurred. Finding ovarian cancer cells in pleural fluid (from the cavity which surrounds the lungs) is also evidence of stage IV disease.

In one embodiment the ovarian cancer is: type I, for example IA, IB or IC; type II, for example IIA, IIB or IIC; type III, for example IIIA, IIIB or IIIC; or type IV.

The present disclosure relates to treatment of any stage of ovarian cancer, in particular as described herein.

Lung cancers are classified according to histological type and are categorized by the size and appearance of the malignant cells seen by a histopathologist under a microscope. For therapeutic purpose, two broad classes are distinguished: non-small cell lung carcinoma and small cell lung carcinoma.

In one embodiment the epithelial cancer is lung cancer, for example small-cell lung cancer (SCLC) and non-small-cell lung cancer (NSCLC).

Non-Small-Cell Lung Carcinoma—

The three main subtypes of NSCLC are adenocarcinoma, squamous-cell carcinoma and large-cell carcinoma.

Nearly 40% of lung cancers are adenocarcinoma, which usually originates in peripheral lung tissue. A subtype of adenocarcinoma, the bronchioloalveolar carcinoma, is more common in female never-smokers, and may have a better long term survival.

Squamous-cell carcinoma accounts for about 30% of lung cancers. They typically occur close to large airways. A hollow cavity and associated cell death are commonly found at the center of the tumour. About 9% of lung cancers are large-cell carcinoma. These are so named because the cancer cells are large, with excess cytoplasm, large nuclei and conspicuous nucleoli.

Small-Cell Lung Carcinoma—

In small-cell lung carcinoma (SCLC), the cells contain dense neurosecretory granules (vesicles containing neuroendocrine hormones), which give this tumour an endocrine/paraneoplastic syndrome association. Most cases arise in the larger airways (primary and secondary bronchi). These cancers grow quickly and spread early in the course of the disease. Sixty to seventy percent have metastatic disease at presentation.

In one embodiment the cancer is non-small lung carcinoma.

In one embodiment there is provided treatment of renal cancer, for example renal cell carcinoma and/or urothelial cell carcinoma using an oncolytic adenovirus as disclosed herein. Other examples of renal cancer include squamous cell carcinoma, juxtaglomerular cell tumour (reninoma), angiomyolipoma, renal oncocytoma, Bellini duct carcinoma, clear-cell sarcoma of the kidney, mesoblastic nephroma, Wilms' tumour, mixed epithelial stromal tumour, clear cell adenocarcinoma, transitional cell carcinoma, inverted papilloma, renal lymphoma, teratoma, carcinosarcoma, and carcinoid tumour of the renal pelvis.

In one embodiment the cancer is bladder cancer, for example is any of several types of malignancy arising from the epithelial lining (i.e., the urothelium) of the urinary bladder. About 90% of bladder cancers are transitional cell carcinoma. The other 10% are squamous cell carcinoma, adenocarcinoma, sarcoma, small cell carcinoma, and secondary deposits from cancers elsewhere in the body. The staging of is given below.

T (Primary Tumour)
TX Primary tumour cannot be assessed
T0 No evidence of primary tumour
Ta Non-invasive papillary carcinoma
Tis Carcinoma in situ ('flat tumour')
T1 Tumour invades subepithelial connective tissue
T2a Tumour invades superficial muscle (inner half)
T2b Tumour invades deep muscle (outer half)
T3 Tumour invades perivesical tissue:
T3a Microscopically
T3b Macroscopically (extravesical mass)
T4a Tumour invades prostate, uterus or vagina
T4b Tumour invades pelvic wall or abdominal wall
N (Lymph Nodes)
NX Regional lymph nodes cannot be assessed
N0 No regional lymph node metastasis
N1 Metastasis in a single lymph node 2 cm or less in greatest dimension
N2 Metastasis in a single lymph node more than 2 cm but not more than 5 cm in greatest dimension, or multiple lymph nodes, none more than 5 cm in greatest dimension
N3 Metastasis in a lymph node more than 5 cm in greatest dimension
M (Distant Metastasis)
MX Distant metastasis cannot be assessed
M0 No distant metastasis
M1 Distant metastasis.

Thyroid cancer as employed herein refers to cancer of the thyroid originating from follicular or parafollicular thyroid cells and includes papillary thyroid cancer (75% to 85% of cases); follicular thyroid cancer (10% to 20% of cases); medullary thyroid cancer (5% to 8% of cases)—cancer of the parafollicular cells, often part of multiple endocrine neoplasia type 2; poorly differentiated thyroid cancer; anaplastic thyroid cancer (less than 5% of cases) is not responsive to treatment and can cause pressure symptoms, thyroid lymphoma, squamous cell thyroid carcinoma, sarcoma of thyroid.

Renal cancer as employed herein refers to cancer of the kidney, for example renal cell carcinoma and transitional cell carcinoma of the renal pelvis, such as squamous cell carcinoma, juxtaglomerular cell tumor (reninoma), angiomyolipoma, renal oncocytoma, bellini duct carcinoma, clear-cell sarcoma of the kidney, mesoblastic nephroma, Wilms' tumor, mixed epithelial stromal tumor, clear cell adenocarcinoma, transitional cell carcinoma, inverted papilloma, renal lymphoma, teratoma, carcinosarcoma; carcinoid tumor of the renal pelvis.

Bladder cancer as employed herein refers to cancer of the bladder including transitional cell bladder cancer, carcinoma in situ, papillary cancer and rarer types of bladder cancer such as squamous cell cancer and adenocarcinoma.

Oesphageal cancer as employed herein refers to cancer of the oesphagus including esophageal squamous-cell carcinomas, esophageal adenocarcinomas, and variants of squamous-cell carcinoma, and non-epithelial tumors, such as leiomyosarcoma, malignant melanoma, rhabdomyosarcoma, lymphoma, among others.

Head and neck cancer as employed herein refers to cancer of the neck and/or head, including mouth cancer, nasopharyngeal cancer, oropharyngeal cancer, paranasal sinus cancer and salivary gland cancer.

Chemotherapeutic Agents

Chemotherapeutic agent and chemotherapy or cytotoxic agent are employed interchangeably herein unless the context indicates otherwise.

Chemotherapy as employed herein is intended to refer to specific antineoplastic chemical agents or drugs that are "selectively" destructive to malignant cells and tissues, for example alkylating agents, antimetabolites including thymidylate synthase inhibitors, anthracyclines, anti-microtubule agents including plant alkaloids, topoisomerase inhibitors, parp inhibitors and other antitumour agents. Selectively in this context is used loosely because of course many of these agents have serious side effects.

The preferred dose may be chosen by the practitioner, based on the nature of the cancer being treated.

Examples of alkylating agents, which may be employed in the method of the present disclosure include an alkylating agent nitrogen mustards, nitrosoureas, tetrazines, aziridines, platins and derivatives, and non-classical alkylating agents.

Example a platinum containing chemotherapeutic agent (also referred to as platins), such as cisplatin, carboplatin, oxaliplatin, satraplatin, picoplatin, nedaplatin, triplatin and lipoplatin (a liposomal version of cisplatin), in particular cisplatin, carboplatin and oxaliplatin.

The dose for cisplatin ranges from about 20 to about 270 mg/m$^2$ depending on the exact cancer. Often the dose is in the range about 70 to about 100 mg/m$^2$.

Nitrogen mustards include mechlorethamine, cyclophosphamide, melphalan, chlorambucil, ifosfamide and busulfan.

Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide.

Aziridines include thiotepa, mytomycin and diaziquone (AZQ).

Examples of antimetabolites, which may be employed in the method of the present disclosure, include anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed(tomudex) hydrochloride, cladribine and 6-azauracil.

Examples of anthracyclines, which may be employed in the method of the present disclosure, include daunorubicin (Daunomycin), daunorubicin (liposomal), doxorubicin (Adriamycin), doxorubicin (liposomal), epirubicin, idarubicin, valrubicin currently used only to treat bladder cancer and mitoxantrone an anthracycline analog, in particular doxorubicin.

Examples of anti-microtubule agents, which may be employed in the method of the present disclosure, include include vinca alkaloids and taxanes.

Vinca alkaloids include completely natural chemicals for example vincristine and vinblastine and also semi-synthetic vinca alkaloids, for example vinorelbine, vindesine, and vinflunine Taxanes include paclitaxel, docetaxel, abraxane, carbazitaxel and derivatives of thereof. Derivatives of taxanes as employed herein includes reformulations of taxanes like taxol, for example in a micelluar formulations, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, indotecan and indimitecan. Type II inhibitors include genistein and ICRF 193 which has the following structure:

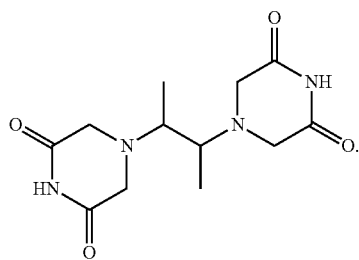 [SMILES: CC(C(C)N1CC(=O)NC(=O)C1)N1CC(=O)NC(=O)C1]

Type II poisons include amsacrine, etoposide, etoposide phosphate, teniposide and doxorubicin and fluoroquinolones.

In one embodiment the chemotherapeutic is a PARP inhibitor.

Combination Therapy

In one embodiment a combination of chemotherapeutic agents employed is, for example a platin and 5-FU or a prodrug thereof, for example cisplatin or oxaplatin and capecitabine or gemcitabine, such as FOLFOX.

In one embodiment the chemotherapy comprises a combination of chemotherapy agents, in particular cytotoxic chemotherapeutic agents.

In one embodiment the chemotherapy combination comprises a platin, such as cisplatin and fluorouracil or capecitabine.

In one embodiment the chemotherapy combination in capecitabine and oxaliplatin (Xelox).

In one embodiment the chemotherapy is a combination of folinic acid and 5-FU, optionally in combination with oxaliplatin.

In one embodiment the chemotherapy is a combination of folinic acid, 5-FU and irinotecan (FOLFIRI), optionally in combination with oxaliplatin (FOLFIRINOX). The regimen consists of: irinotecan (180 mg/m$^2$ IV over 90 minutes) concurrently with folinic acid (400 mg/m$^2$ [or 2×250 mg/m$^2$] IV over 120 minutes); followed by fluorouracil (400-500 mg/m$^2$ IV bolus) then fluorouracil (2400-3000 mg/m$^2$ intravenous infusion over 46 hours). This cycle is typically repeated every two weeks. The dosages shown above may vary from cycle to cycle.

In one embodiment the chemotherapy combination employs a microtubule inhibitor, for example vincristine sulphate, epothilone A, N-[2-[(4-Hydroxyphenyl)amino]-3-pyridinyl]-4-methoxybenzenesulfonamide (ABT-751), a taxol derived chemotherapeutic agent, for example paclitaxel, abraxane, or docetaxel or a combination thereof.

In one embodiment the chemotherapy combination employs an mTor inhibitor. Examples of mTor inhibitors include: everolimus (RAD001), WYE-354, KU-0063794, papamycin (Sirolimus), Temsirolimus, Deforolimus (MK-8669), AZD8055 and BEZ235(NVP-BEZ235).

In one embodiment the chemotherapy combination employs a MEK inhibitor. Examples of MEK inhibitors include: AS703026, CI-1040 (PD184352), AZD6244 (Selumetinib), PD318088, PD0325901, AZD8330, PD98059, U0126-EtOH, BIX 02189 or BIX 02188.

In one embodiment the chemotherapy combination employs an AKT inhibitor. Examples of AKT inhibitors include: MK-2206 and AT7867.

In one embodiment the combination employs an aurora kinase inhibitor. Examples of aurora kinase inhibitors include: Aurora A Inhibitor I, VX-680, AZD1152-HQPA (Barasertib), SNS-314 Mesylate, PHA-680632, ZM-447439, CCT129202 and Hesperadin.

In one embodiment the chemotherapy combination employs a p38 inhibitor, for example as disclosed in WO2010/038086, such as N-[4-({4-[3-(3-tert-Butyl-1-p-tolyl-1H-pyrazol-5-yl)ureido]naphthalen-1-yloxy}methyl) pyridin-2-yl]-2-methoxyacetamide.

In one embodiment the combination employs a Bcl-2 inhibitor. Examples of Bcl-2 inhibitors include: obatoclax mesylate, ABT-737, ABT-263(navitoclax) and TW-37.

In one embodiment the chemotherapy combination comprises an antimetabolite such as capecitabine (xeloda), fludarabine phosphate, fludarabine (fludara), decitabine, raltitrexed (tomudex), gemcitabine hydrochloride and cladribine.

In one embodiment the chemotherapy combination comprises ganciclovir, which may assist in controlling immune responses and/or tumour vasculation.

In one embodiment the chemotherapy includes a PARP inhibitor.

In one embodiment the chemotherapy includes an inhibitor of cancer metabolism with specific inhibition of the activity of the DHODH enzyme.

In one embodiment one or more therapies employed in the method herein are metronomic, that is a continuous or frequent treatment with low doses of anticancer drugs, often given concomitant with other methods of therapy.

In one embodiment, there is provided the use of multiple cycles of treatment (such as chemotherapy) for example 2, 3, 4, 5, 6, 7, 8.

In one embodiment the chemotherapy is employed in a 28 day cycle.

"Comprising" in the context of the present specification is intended to mean "including". Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The invention will now be described with reference to the following examples, which are merely illustrative and should not in any way be construed as limiting the scope of the present invention.

BRIEF SUMMARY OF THE FIGURES

FIG. 2 Shows patient data for 46 year old female who received 400 mg Valitinib BID and cisplatin/capecitabine chemotherapy.

FIG. 3 Shows patient data for 56 year old male who received 400 mg Valitinib BID and cisplatin/capecitabine chemotherapy.

FIG. 4 Shows patient data for 60 year old male who received 500 mg Valitinib BID and cisplatin/capecitabine chemotherapy.

FIG. 5 Shows patient data for Example 4 a 57 year old male who received 300 mg Valitinib BID and oxaliplatin/capecitabine chemotherapy.

FIG. 6a Shows the patients in the Varlitinib Phase Ib trial-Taiwan.

FIG. 6b Shows the patients in the Varlitinib Phase Ib trial-Taiwan.

FIG. 7a Shows the change in lesion size for individual patients over time in the Taiwan trial.

FIG. 7b Shows the change in lesion size for individual patients over time in the Singapore trial.

FIG. 8a Shows the maximal percentage change in tumour size from baseline for individual patients, Taiwan trial.

FIG. 8b Shows the maximal percentage change in tumour size from baseline for individual patients, Singapore trial. All patients received 300-400 mg ASLAN001 and doublet chemotherapy. Most patients had received at least 2 prior treatments, including XELOX, XELIRI, Gem/Cis, Herceptin etc. Not all patients have completed 4 cycles of therapy. Trial includes 13 patients: 3 PR, 8 SD, 2 PD (23% response rate, 85% disease control)

FIG. 9 Shows the phase 2A/B breast cancer study with Valitinib and Capecitabine or Lapatinib and Capecitabine. While on LAPATINIB: 6 PR, 10 SD, 2 PD; while on ASLAN001: 1 CR, 5 PR, 4 SD, 1 PD, 1 death (no measurement for death case).

FIG. 10 Shows a waterfall plot of the best response of evaluable subjects for the phase 2A/B breast cancer study with Valitinib and Capecitabine or Lapatinib and Capecitabine.

FIG. 11 Shows responses for all subjects for the phase 2A/B breast cancer study with Valitinib and Capecitabine or Lapatinib and Capecitabine. While on LAPATINIB: 1 CR, 6 PR, 13 SD, 1 PD; while on ASLAN001: 1 CR, 7 PR, 6 SD, 1 death (no measurement for death case).

FIG. 12 Shows the days on drug for individual patients in the Singapore trial.

FIG. 13 Show the trial design for the Valitinib neoadjuvant breast cancer study.

EXAMPLES

Figure 1:
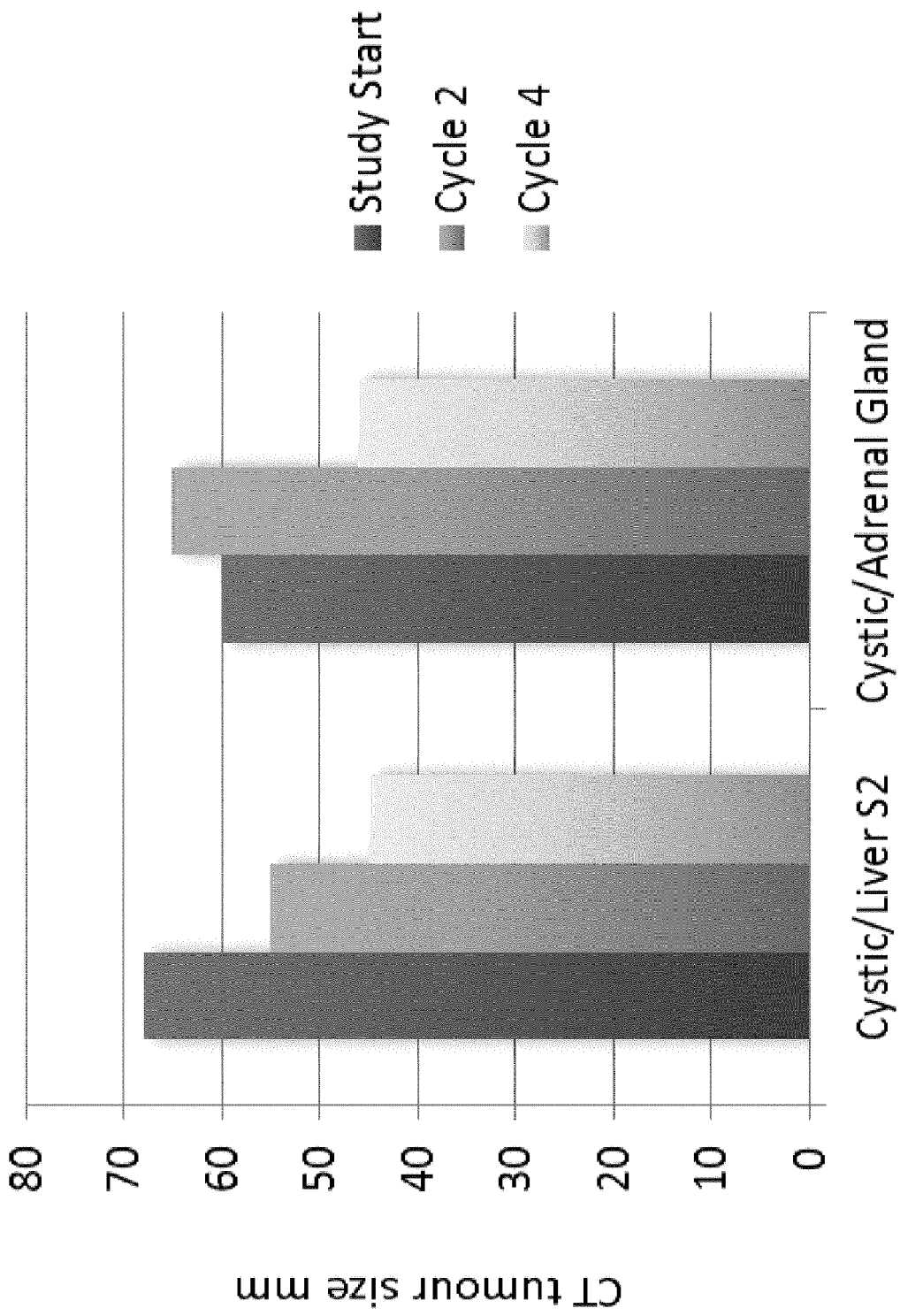
FIG. 1 Shows patient data for 78 year old male who received 400 mg Valitinib BID and cisplatin/capecitabine chemotherapy.

Example 1 Treatment of Gastric Cancer with Valitinib 400 mg Bi-Daily Orally and Cisplatin/Capecitabine Combination Chemotherapy A 78 year-old male with Her2 positive (3+) stage IV gastric cancer had progressive disease in the form of 2 target lesions following:
 first line treatment with cisplatin and Xeloda® (capecitabine)—4 cycles,
 second line treatment with the experimental drug TDM1 (an antibody drug conjugate comprising Herceptin®)—9 cycles,
 third line treatment with experimental drug LJM716 (a Her3 monoclonal antibody) and
 Herceptin®.

After treatment cycle 4 with ASLAN001 400 mg bi-daily, cisplatin and capecitabine, see FIG. 1. No dose limiting toxicity was observed in the first two treatment cycles. ASLAN001 was well tolerated. The cisplatin and capecitabine regime was cisplatin 80 mg/m$^2$ IV infusion and capecitabine 1000 mg/m$^2$ orally twice daily for 14 days every 3 weeks.

A 46 year-old female with gastric cancer (4 target lesions) was given first line treatment of Valitinib 400 mg bi-daily, cisplatin and capecitabine. No dose limiting toxicity was observed in the first two treatment cycles. Varlitinib was well tolerated. The cisplatin and capecitabine regime was cisplatin 80 mg/m$^2$ IV infusion and capecitabine 1000 mg/m$^2$ orally twice daily for 14 days every 3 weeks. The patient showed a 41% response after cycle 4, see FIG. 2. Despite the excellent response the patient was designated with progression disease due to the development of a new bone lesion.

Example 2 Treatment of Cholangiocarcinoma with Varlitinib 400 mg Bi-Daily Orally and Cisplatin/Capecitabine Combination Chemotherapy A 56 year-old male with stage IV cholangiocarcinoma (3 lesions) had progressive disease following treatment with:
 radiotherapy, and
 gemcitabine (Gemzar®) and cisplatin-6 months.

After treatment cycle 6 with Varlitinib 400 mg bi-daily, cisplatin and capecitabine the patient showed an 85.77% response, see FIG. 3. No dose limiting toxicity was observed in the first two treatment cycles. Varlitinib was well tolerated. The cisplatin and capecitabine regime was cisplatin 80 mg/m$^2$ IV infusion and capecitabine 1000 mg/m$^2$ orally twice daily for 14 days every 3 weeks.

Example 3 Treatment of Cholangiocarcinoma with Varlitinib 500 mg Bi-Daily Orally and Cisplatin/Capecitabine Combination Chemotherapy A 60 year-old male with stage IV cholangiocarcinoma had progressive disease following treatment with radiotherapy and bi-weekly 5-FU.

After treatment cycle 2 with Varlitinib orally 500 mg bi-daily, cisplatin and capecitabine the patient showed a 4% response, see FIG. 4. The cisplatin and capecitabine regime was cisplatin 80 mg/m² IV infusion and capecitabine 1000 mg/m² orally twice daily for 14 days every 3 weeks.

Example 4 Treatment of Stage IV Sigmoid Coloreactal Cancer with Varlitinib 300 mg BID Oxaliplatin/Capecitabine A 57 year-old male with stage IV sigmoid colorectal cancer with metastasis to liver, lungs and lymph node.
The prior treatments included:
Anterior resection with right hemi-hepatetomy and cholecystecomy
XELOX (PD), XELIRI (PR), Irrinotecan & Cetuximab (SD)
Xeloda and Avastin (SD), Bayer PTEFb-CDK9 inhibitor (PD)
The treatment per 3 weeks cycle was 300 mg ASLAN001 orally bi-daily, oxaliplatin 130 mg/m² IV infusion (Day 1) and capecitabine 850 mg/m² (Day 1-14) until Cycle 6, then from Cycle 7+ onwards, Varlitinib 300 mg b-daily as monotherapy per 4 week cycle.
After 2 cycles oxaliplatin/capecitabine+Valitinib showed a 335 partial response the results are shown in FIG. 5.

Example 5 Treatment of Stage IV Cholangiocarcinoma and Metastatic Lymphadenopathy with Varlitinib 400 mg Bi-Daily Orally and Cisplatin/5FU Combination Chemotherapy A 49 year-old male with stage IV Cholangiocarcinoma and metastatic lymphadenopathy diagnosed in January 2016, no prior surgery or treatment was give first line treatment of 300 mg BID Varlitinib combined with Cis/5-FU, 28-day cycle.
Date of the first response 5 Mar. 2016, tumor C2 was reduced by 16%. Last response tumor C4 was reduced by 13% (17 May 2016). Patient current disease status is stable disease.

Example 6 Treatment of the Intrahepatic Bile Duct Cholangiocarcinoma with 300 mg Valitinib and FOLFOX A 51 year old female diagnosed in 2013 with intrahepatic bile duct cholangiocarcinoma, had received surgery in the form of left hemihepatectomy in 15 Jul. 2013. Prior therapies were gemcitabine and cisplatin 14 Aug. 2013 with last dose 8 Jan. 2014 and repeated between 13 May 2015 and 1 Jul. 2015. With this treatment the status was progressive disease. The patient was give 9 cycles combination Varlitinib 400 mg reduced to 300 mg BID and FOLFOX. This was followed with 7 cycles of Valitinib monotherapy. The patient status is partial response with a reduction is tumor size of 50%.

Example 7 Treatment of the Bladder Cancer with 300 mg Valitinib and FOLFOX

A 63 year old male was diagnosed with bladder cancer 2014. He received radical cystoprostatetomy and prior therapy with Cisplatin and radiotherapy (pelvis) on 20 Feb. 2014; gemcitabline and cisplatin on 10 Apr. 2015 with last dose on 8 May 2015.
The patient received 9 cycles of 300 mg Valitinib BID and FOLFOX and 5 cycles of Varlitinib 300 mg monotherapy. The Valitinib in the combination therapy interruption from 21 to 27 Sep. 2015; 21 Oct. to 23 Oct. 2015; 4 days on and 3 days off—due to G2 weight loss. The patient status is stable disease with best % tumour change of −4%.

Example 8 Treatment of Stage IV Intrahepatic Cholangiocarcinoma and Multiple Lymphadenopathies with Valitinib 300 mg Bi-Daily Orally and Cisplatin/5FU Combination Chemotherapy 28 Day Cycle A 64 year old female diagnosed with intrahepatic cholangiocarcinoma and multiple lymphadenopathies in May 2016 received Valitinib combination therapy as the first line treatment
The patient was given 300 mg BID Varlitinib combined with Cis/5-FU, 28-day cycle. The current status is the clinical trial is on-going.
As of June 2016 the following clinical data summary:

| Arm | Dose of Varlitinib | Patients | Best response |
|---|---|---|---|
| Combo with cis/cap | 400 mg (closed) | 6 | PR (−87%) |
|  | 500 mg (closed) | 4 | SD (−4%) |
| Combo with cis/5-FU | 400 mg (stopped) | 7 | PR (−47%) |
|  | 300 mg (recruiting) | 6 | SD (−21%) |

The invention claimed is:

1. A method of treatment comprising administering a combination therapy to a human cancer patient comprising;
   a) a therapeutically effective amount of a compound of formula (I):

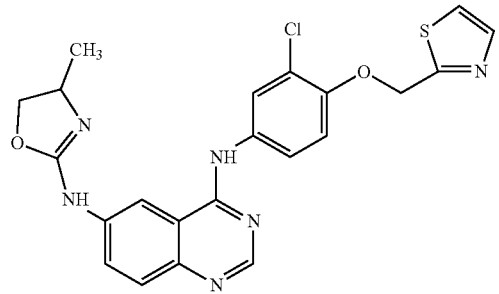 [SMILES: CC1COC(Nc2ccc3ncnc(Nc4ccc(OCc5nccs5)c(Cl)c4)c3c2)=N1]

an enantiomer thereof or a pharmaceutically acceptable salt of any one of the same, and
   b) a chemotherapeutic agent or a combination of chemotherapeutic agents comprising a pyrimidine analogue;
   wherein administering the combination therapy sensitizes the patient to the chemotherapeutic agent or combination of chemotherapeutic agents; and
   wherein the patient has a cancer independently selected from gastric cancer, cholangiocarcinoma, colorectal cancer and bladder cancer.

2. A method according to claim 1, wherein the compound of formula (I) is:

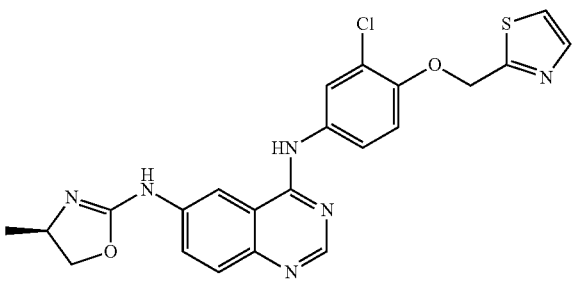 [SMILES: C[C@@H]1COC(Nc2ccc3ncnc(Nc4ccc(OCc5nccs5)c(Cl)c4)c3c2)=N1]

or a pharmaceutically acceptable salt thereof.

3. A method according to claim 1, wherein the compound of formula (I) is provided as the free base.

4. A method according to claim 1, wherein the pyrimidine analogue is selected from the group comprising 5-fluorouracil (5-FU), capecitabine (Xeloda®), floxuridine, gemcitabine, cytarabine, decitabine, raltitrexed (tomudex) hydrochloride, cladribine and 6-azauracil.

5. A method according to claim 1, wherein the pyrimidine analogue is 5-FU.

6. A method according to claim 1, wherein the pyrimidine analogue is gemcitabine.

7. A method according to claim 1, wherein the pyrimidine analogue is capecitabine.

8. A method according to claim 1, wherein the chemotherapeutic agent or combination of chemotherapeutic agents is selected from FOLFOX, GEMOX, FOLFIRI and FOLFIRINOX.

9. A method according to claim 1, wherein the combination therapy further comprises a platinum based chemotherapeutic agent.

10. A method according to claim 9, wherein the platinum based chemotherapeutic agent is selected from the group comprising cisplatin, carboplatin, oxaliplatin, satraplatin, picoplatin, nedaplatin, triplatin, lipoplatin and combinations thereof.

11. A method according to claim 1, wherein the combination therapy further comprises cisplatin.

12. A method according to claim 1, wherein the combination therapy further comprises oxaliplatin.

13. A method according to claim 1, wherein the cancer is cholangiocarcinoma.

14. A method according to claim 1, wherein the patient has a cancer that is refractory and/or resistant to chemotherapy.

15. A method according to claim 1, wherein the patient has a cancer that is HER2 positive or HER2 amplified.

16. A method according to claim 1, wherein each dose of the compound of formula (I) is in the range 100 to 900 mg.

17. A method according to claim 1, wherein the compound of formula (I) is administered as a pharmaceutical composition comprising one or more pharmaceutically acceptable excipients.

18. A method according to claim 1, wherein the compound of formula (I) or a pharmaceutical composition comprising the same is administered orally.

19. A method according to claim 1, wherein the compound of formula (I) or a pharmaceutical composition thereof is administered bi-daily.

* * * * *